US010100010B1

(12) United States Patent
Lee et al.

(10) Patent No.: US 10,100,010 B1
(45) Date of Patent: Oct. 16, 2018

(54) 4-METHOXY PYRROLE DERIVATIVES OR SALTS THEREOF AND PHARMACEUTICAL COMPOSITION COMPRISING THE SAME

(71) Applicant: Daewoong Pharmaceutical Co., Ltd., Gyeonggi-do (KR)

(72) Inventors: Chun Ho Lee, Seoul (KR); Seung Chul Lee, Gyeonggi-do (KR); Yeon Im Lee, Gyeonggi-do (KR); Deok Ki Eom, Gyeonggi-do (KR); Mi Ryeong Han, Gyeonggi-do (KR); Eun Ji Koh, Gyeonggi-do (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 72 days.

(21) Appl. No.: 15/520,518

(22) PCT Filed: Apr. 27, 2016

(86) PCT No.: PCT/KR2016/004411
§ 371 (c)(1),
(2) Date: Apr. 20, 2017

(87) PCT Pub. No.: WO2016/175555
PCT Pub. Date: Nov. 3, 2016

(30) Foreign Application Priority Data

Apr. 27, 2015 (KR) .................. 10-2015-0058712
Feb. 3, 2016 (KR) .................. 10-2016-0013588

(51) Int. Cl.
*C07D 207/48* (2006.01)
*A61P 31/04* (2006.01)
*A61P 1/16* (2006.01)

(52) U.S. Cl.
CPC .............. *C07D 207/48* (2013.01); *A61P 1/16* (2018.01); *A61P 31/04* (2018.01)

(58) Field of Classification Search
CPC .................................................. C07D 207/48
See application file for complete search history.

(56) References Cited

U.S. PATENT DOCUMENTS

2008/0139639 A1* 6/2008 Kajino ............... A61K 31/4025
514/423

FOREIGN PATENT DOCUMENTS

| CN | 104447191 A | 3/2015 |
|----|-------------|--------|
| JP | 2010-520153 A | 6/2010 |
| KR | 10-2007-0060133 | 6/2007 |
| KR | 10-2009-0013815 A | 2/2009 |
| KR | 10-0941527 B1 | 2/2010 |
| KR | 10-2010-0134667 A | 12/2010 |
| KR | 10-2011-0010841 A | 2/2011 |
| KR | 10-2011-0091826 | 8/2011 |
| KR | 10-2013-0055610 A | 5/2013 |
| KR | 10-2015-0143439 A | 12/2015 |
| WO | WO-03/040147 A1 | 5/2003 |
| WO | WO-2004/014368 A1 | 2/2004 |
| WO | WO-2006/023462 A1 | 3/2006 |
| WO | WO-2006/025716 A1 | 3/2006 |
| WO | WO-2006/036024 A1 | 4/2006 |
| WO | WO-2007/072146 A1 | 6/2007 |
| WO | WO-2014/075575 A1 | 5/2014 |
| WO | WO-2015/075575 A1 | 5/2015 |
| WO | WO-2015/134539 A1 | 9/2015 |

OTHER PUBLICATIONS

Arikawa et al., "Synthetic Studies of Five-Membered Heteroaromatic Derivatives as Potassium-Competitive Acid Blockers (P-CABs)," Bioorganic & Medicinal Chemistry Letters, 25:2037-2040 (2015).
Blangetti et al., LIC-KOR-Promoted Synthesis of Alkoxydienyl Amines: An Entry to 2,3,4,5-Tetrasubstituted Pyrroles, *Organic Letters*, 11(17):3914-3917 (2009).
Chiou et al., "Survivin: A Novel Target for Indomethacin-Induced Gastric Injury," *Gastroenterology*, 128:63-73 (2005).
Glennon et al., "Serotonin Receptor Subtypes and Ligands," *Psychopharmacology—The Fourth Generation of Progress* (2000).
International Search Report and Written Opinion for Application No. PCT/KR2016/004411, dated Jan. 16, 2017.
Mohammad-Zadeh et al., "Serotonin: A Review," *J. Vet. Pharmacol. Ther.*, 31(3):187-199 (2008).
Nishida et al., "Discovery, Synthesis, and Biological Evaluation of Novel Pyrrole Derivatives as Highly Selective Potassium-Competitive Acid Blockers," *Bioorganic & Medicinal Chemistry*, 20:3925-3938 (2012).
Rabon et al., "Preparation of Gastric $H^+,K^+$-ATPase," *Methods Enzymol.*, 157:649-654 (1988).
Tan et al., "Gastric Cytoprotective Anti-Ulcer Effects of the Leaf Methanol Extract of *Ocimum suave* (Lamiaceae) in Rats," *Journal of Ethnopharmacology*, 82:69-72 (2002).

* cited by examiner

*Primary Examiner* — Laura L Stockton
(74) *Attorney, Agent, or Firm* — Marshall, Gerstein & Borun LLP

(57) ABSTRACT

The present invention provides a 4-methoxy pyrrole derivative or a pharmaceutically acceptable salt thereof, a preparation method thereof, and a pharmaceutical composition containing the same. The 4-methoxy pyrrole derivatives or pharmaceutically acceptable salts thereof according to the present invention have not only excellent proton pump inhibitory activity, gastric damage-inhibiting activity and defensive factor-enhancing effects, but also excellent eradication activity against *H. pylori*. Therefore, the 4-methoxy pyrrole derivatives or pharmaceutically acceptable salts thereof can be effectively used for the prevention and treatment of gastrointestinal damage due to gastrointestinal tract ulcer, gastritis, reflux esophagitis or *H. pylori*. Moreover, the 4-methoxy pyrrole derivatives or pharmaceutically acceptable salts thereof, have inhibitory activities against GPCR and thus can be effectively used for the prevention and treatment of 5-HT receptor-mediated or muscarinic acetylcholine receptor-mediated diseases.

16 Claims, No Drawings

4-METHOXY PYRROLE DERIVATIVES OR SALTS THEREOF AND PHARMACEUTICAL COMPOSITION COMPRISING THE SAME

TECHNICAL FIELD

The present invention relates to a 4-methoxy pyrrole derivative or a pharmaceutically acceptable salt thereof and a pharmaceutical composition containing the same.

BACKGROUND OF ART

Gastrointestinal tract ulcer, gastritis, and reflux esophagitis are generated while the balance between offensive factors (for example, gastric acid, *Helicobacter* bacteria pepsin, stress, alcohol and tobacco, etc.) and defensive factors (for example, gastric mucosa, bicarbonate, prostaglandin, the degree of blood supply, etc.) is destroyed. Therefore, a therapeutic agent for treating gastrointestinal damage such as gastrointestinal tract ulcer, gastritis and reflux esophagitis is divided into a drug for inhibiting the offensive factors and a drug for enhancing the defensive factors. As the drug for inhibiting the offensive factors, an antacid, an anticholinergic drug, a $H_2$ receptor antagonist, a proton pump inhibitor (PPI), an acid pump antagonist (APA) also referred to as a reversible proton pump inhibitor, and the like have been known. For example, as drugs having gastric acid pump antagonistic activity, WO2006/025716 discloses pyrrolo[2,3-c]pyridine derivatives, and WO2007/072146 discloses benzimidazole derivatives. In addition, WO2006/036024 discloses pyrrole derivatives having a reversible proton pump inhibitory activity.

On the other hand, it is reported that gastrointestinal tract ulcer, gastritis, and reflux esophagitis occur ulcers even without an increase in secretion of gastric acid. Thus, as much as the offensive factor increases, a reduction in the defensive factor due to a pathological change of the gastric mucosa is thought to play an important role in the occurrence of gastric ulcers. Thus, in addition to drugs for inhibiting the offensive factors, drugs for enhancing the defensive factors are used for the treatment of gastrointestinal tract ulcer and gastritis. As the drugs for enhancing the defensive factors, mucosal protective drugs which are attached to the ulcer site to form a physicochemical membrane, and drugs that promote the synthesis and secretion of mucus have been known.

On the other hand, *Helicobacter pylori* (*H. pylori*), which is a bacteria present in the stomach, has been known to cause chronic gastritis, gastric ulcer, duodenal ulcer and the like, and a large number of patients with gastrointestinal damages are infected with *H. pylori*. Therefore, these patients must take antibiotics such as clarithromycin, amoxicillin, metronidazole, tetracycline, together with anti-ulcer agents such as a proton pump inhibitor, or an acid pump antagonist. Consequently, various side effects have been reported.

Therefore, there is a need to develop anti-ulcer drugs which inhibit the secretion of gastric acid (for example, proton pump inhibitory activity) and enhance defensive factors (for example, an increase in mucus secretion) and at the same time have eradication activity against *H. pylori*.

Further, studies for G-protein coupled receptor (GPCR) that can cause several diseases have also been performed.

Specifically, 5-hydroxytryptamine (5-HT, serotonin) is an effective factor of gastrointestinal tract, a regulator of platelet and a neurotransmitter of central nervous system, derived from tryptophan, and it can influence on almost all physiological and behavioral functions such as emotion, appetite, cognition, vomiting, endocrine system function, digestive system function, motor function, neurotrophic, perception, sensation function, sex, sleep and cardiovascular function.

Like this, 5-HT is involved in various functions, and the reason has been known to be due to 5-HT cell bodies that are clustered in the brainstem raphe nuclei, an anatomical structure of serotonergic system having a huge neurite that influence on all area of central nervous system neuraxis, a molecular diversity of various 5-HT receptor subtypes present in the cell membrane, and a characteristic cytological distribution (Mohammad-Zadeh, L. F.; Moses, L.; Gwaltney-Brant, S. Serotonin: a review. J. Vet. Pharmacol. Therap. (2008) 31, 187-199, Glennon, R. A.; Dukat, M.; Westkaemper, R. B. Psychopharmacology—The Fourth Generation of Progress).

These 5-HT receptors are classified into seven families (5-HT1 to 5-HT7) including 14 receptor subtypes, depending on the structural, functional and pharmacological standards, among which, except for 5-HT3 receptor which is the opening/closing passage of ligand, all of the receptors correspond to GPCR. In particular, 5-HT2 receptors are classified into 5-HT2A, 5-HT2B, and 5-HT2C receptors, and all of these receptors increase the production of inositol 1,4,5-triphosphate (IP3) by activating phospholipase C (PLC). Thus, recently, most of the drugs that are used for the treatment of psychiatric disorders (for example, depression, manic depression, schizophrenia, autism, obsessive-compulsive neurosis, anxiety disorder, etc.) have been known to act through the serotonergic mechanism. Further, it is reported that diseases such as migraine, hypertension, eating disorders, and irritable bowel syndrome (IBS) are also associated with 5-HT.

On the other hand, acetylcholine is a neurotransmitter of autonomic nervous system and acts on both the central nervous system and the peripheral nervous system, thereby affecting brain and muscular system. Such acetylcholine receptor can be divided into nicotinic acetylcholine receptor (nAChR) as an ionic receptor and a muscarinic acetylcholine receptor (mAChR) as a metabolite receptor. Among them, the muscarinic acetylcholine receptor (mAChR) was identified to include five distinct receptor subtypes, each of which are referred to as M1 to M5 receptors, and these also correspond to GPCR.

In particular, M1 receptors are present in the cerebral cortex of the hippocampus, and involved in the autonomic nerve, salivary gland, gastric secretion and the like. M2 receptors are present in heart, brain cortex and hippocampus, and involved in a decrease of heart rate, a reduction of atrial contraction force, a decrease in the conduction velocity of AV node, and the like. Specifically, when exposed to acetylcholine for up to few seconds, the cortex pyramidal neurons are inhibited through M1 muscarinic receptor linked to an alpha subunit of Gq-type G proteins. Therefore, when the M1 receptor is activated, the calcium stored in the cell is released to occur potassium conduction activated by the release of calcium, thereby the spiking of pyramidal neurons can be inhibited.

By inhibiting the action of these M1 and M2 receptors, various diseases can be prevented or treated. Specifically, as the therapeutic agents for inhibiting the action of M1 receptors, a therapeutic agent for the treatment of a peptic ulcer such as pirenzepine using the effects of preventing the secretion of gastric acid and reducing the stomach cramps, a therapeutic agent for the treatment of diabetic neuropathy using the effect of reducing a nerve conduction velocity and preventing a tactile allodynia and thermal hypoalgesia, and the like have been known. As the therapeutic agents for inhibiting the action of M2 receptors, a therapeutic agent for the treatment of overactive bladder using the effects of inhibiting allergic reactions induced by M2 receptors, a therapeutic agent for the treatment of asthma, and the like have been known. Therefore, it appears that the muscarinic acetylcholine antagonist is likely to be developed as a therapeutic agent for the treatment of diseases such as peptic ulcer, diabetic neuropathy, asthma, and overactive bladder.

Consequently, in order to prevent and treat diseases associated with 5-HT and acetylcholine, it is necessary to study compounds which can exhibit an inhibitory action on their GPCR, particularly 5-HT2A, M1 and M2 muscarinic receptors.

Given the above circumstances, the present inventors have conducted numerous studies and found that 4-methoxy pyrrole derivatives or pharmaceutically acceptable salts thereof have excellent anti-ulcer activity (i.e., proton pump inhibitory activity, etc.) and eradication activity against *H. pylori* and thus are useful in the prevention and treatment of gastrointestinal damage due to gastrointestinal tract ulcer, gastritis, reflux esophagitis or *H. pylori*. In addition, the present inventors have found that these 4-methoxy pyrrole derivatives or pharmaceutically acceptable salts thereof have inhibitory activities against GPCRs that cause diseases, for example, 5-HT2A, M1 and M2 muscarinic receptors and the like, and thus can be effectively used for the prevention and treatment of 5-HT receptor or muscarinic acetylcholine receptor-mediated diseases. The present invention has been completed on the basis of such a finding.

DETAILED DESCRIPTION OF THE INVENTION

Technical Problem

It is an object of the present invention to provide a 4-methoxy pyrrole derivative or a pharmaceutically acceptable salt thereof and a pharmaceutical composition comprising the same.

Technical Solution

In accordance with an embodiment of the present invention, there is provided a 4-methoxy pyrrole derivative or a pharmaceutically acceptable salt thereof, having anti-ulcer activity (i.e., proton pump inhibitory activity, etc.), eradication activity against *H. pylori* and inhibitory activity against GPCR.

In accordance with an embodiment of the present invention, there are provided a pharmaceutical composition for the prevention and treatment of gastrointestinal damage due to gastrointestinal tract ulcer, gastritis, reflux esophagitis or *H. pylori*, comprising the above-mentioned compound or a pharmaceutically acceptable salt thereof.

In accordance with an embodiment of the present invention, there is provided a pharmaceutical composition for the prevention and treatment of 5-HT receptor-mediated or muscarinic acetylcholine receptor-mediated diseases, comprising the above-mentioned compound or a pharmaceutically acceptable salt thereof.

Advantageous Effects

The compounds according to the present invention, that is, 4-methoxy pyrrole derivatives or pharmaceutically acceptable salts thereof, have not only excellent proton pump inhibitory activity, gastric damage-inhibiting activity and defensive factor-enhancing effects, but also excellent eradication activity against *H. pylori*. Therefore, the 4-methoxy pyrrole derivatives or pharmaceutically acceptable salts thereof can be effectively used for the prevention and treatment of gastrointestinal damage due to gastrointestinal tract ulcer, gastritis, reflux esophagitis or *H. pylori*. Moreover, the compounds according to the present invention, that is, 4-methoxy pyrrole derivatives or pharmaceutically acceptable salts thereof, have inhibitory activities against GPCR and thus can be effectively used for the prevention and treatment of 5-HT receptor-mediated or muscarinic acetylcholine receptor-mediated diseases.

DETAILED DESCRIPTION OF THE EMBODIMENTS

The present invention provides a compound represented by the following Chemical Formula 1 or a pharmaceutically acceptable salt thereof:

[Chemical Formula 1]

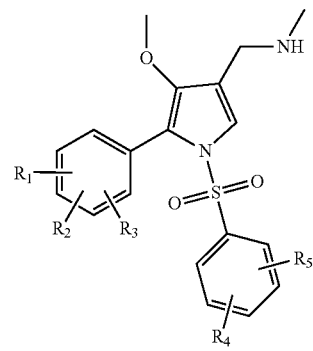

in Chemical Formula 1, $R_1$, $R_2$ and $R_3$ are each independently hydrogen, or halogen, $R_4$ and $R_5$ are each independently hydrogen, halogen, $C_{1-4}$ alkyl, $C_{1-4}$ alkoxy, $C_{1-4}$ haloalkyl, or $C_{1-4}$ haloalkoxy, with the proviso that $R_1$, $R_2$ and $R_3$ cannot be hydrogen simultaneously, and $R_4$ and $R_5$ cannot be hydrogen simultaneously.

Preferably, $R_1$, $R_2$ and $R_3$ are each independently hydrogen, fluoro, or chloro.

Also preferably, $R_4$ and $R_5$ are each independently hydrogen, chloro, fluoro, methyl, trifluoromethyl, methoxy, or difluoromethoxy.

In accordance with an embodiment, the above-mentioned compounds can be represented by the following Chemical Formula 1-1:

[Chemical Formula 1-1]

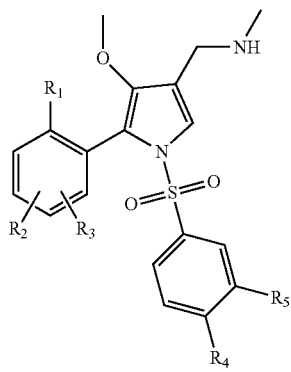

in Chemical Formula 1-1, $R_1$, $R_2$ and $R_3$ may be each independently hydrogen, or halogen. However, $R_1$, $R_2$ and $R_3$ cannot be hydrogen simultaneously.

Preferably, $R_1$, $R_2$ and $R_3$ are each independently hydrogen, fluoro, or chloro.

Also preferably, $R_1$ is halogen, and $R_2$ and $R_3$ are each independently hydrogen, or halogen.

Further preferably, $R_1$ is fluoro, and $R_2$ and $R_3$ are each independently hydrogen, fluoro, or chloro; or $R_1$ is chloro and $R_2$ and $R_3$ may be hydrogen.

In Chemical Formula 1-1, $R_4$ and $R_5$ are each independently hydrogen, halogen, $C_{1-4}$ alkyl, $C_{1-4}$ alkoxy, $C_{1-4}$ haloalkyl, or $C_{1-4}$ haloalkoxy. However, $R_4$ and $R_5$ cannot be hydrogen simultaneously.

Preferably, $R_4$ and $R_5$ are each independently hydrogen, chloro, fluoro, methyl, trifluoromethyl, methoxy, or difluoromethoxy.

Also preferably, $R_4$ is hydrogen, $R_5$ is chloro, fluoro, methyl, trifluoromethyl, methoxy, or difluoromethoxy; or $R_4$ and $R_5$ may be each independently chloro or fluoro.

Further preferably, $R_1$ is fluoro, and $R_2$ and $R_3$ are each independently hydrogen, or fluoro, $R_4$ is hydrogen, and $R_5$ may be chloro, or trifluoromethyl.

In accordance with an embodiment, the above-mentioned compounds can be selected from the group represented by the following Chemical Formulae 1-2 to 1-4, but are not limited thereto:

[Chemical Formula 1-2]

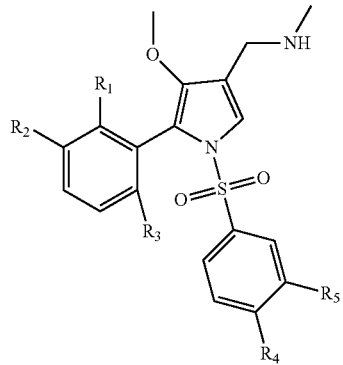

[Chemical Formula 1-3]

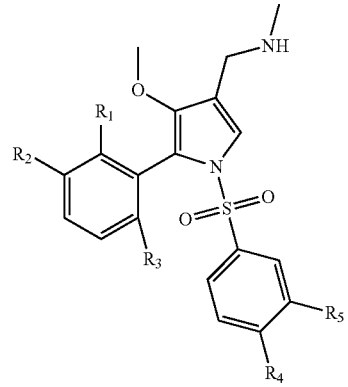

[Chemical Formula 1-4]

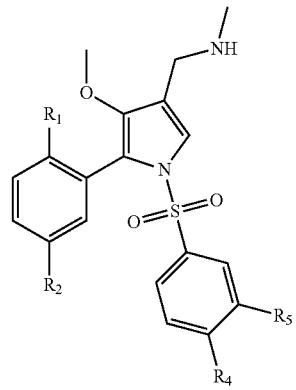

in Chemical Formulae 1-2 to 1-4, $R_1$ to $R_5$ are as defined above.

In accordance with an embodiment, the above-mentioned compound is selected from the group consisting of the following compounds:

1) 1-(5-(2-fluorophenyl)-4-methoxy-1-((3-chlorophenyl)sulfonyl)-1H-pyrrol-3-yl)-N-methylmethanamine;
2) 1-(5-(2-fluorophenyl)-4-methoxy-1-((3-(trifluoromethyl)phenyl)sulfonyl)-1H-pyrrol-3-yl)-N-methylmethanamine;
3) 1-(5-(2-fluorophenyl)-4-methoxy-1-((3-methoxyphenyl)sulfonyl)-1H-pyrrol-3-yl)-N-methylmethanamine;
4) 1-(5-(2-fluorophenyl)-4-methoxy-1-((3-difluoromethoxyphenyl)sulfonyl)-1H-pyrrol-3-yl)-N-methylmethanamine;
5) 1-(5-(2-chlorophenyl)-4-methoxy-1-((3-methoxyphenyl)sulfonyl)-1H-pyrrol-3-yl)-N-methylmethanamine;
6) 1-(5-(2-fluoro-4-chlorophenyl)-4-methoxy-1-((3-chlorophenyl)sulfonyl)-1H-pyrrol-3-yl)-N-methylmethanamine;
7) 1-(5-(2-fluoro-4-chlorophenyl)-4-methoxy-1-((3-(trifluoromethyl)phenyl)sulfonyl)-1H-pyrrol-3-yl)-N-methylmethanamine;
8) 1-(5-(2,4-difluorophenyl)-1-((3-fluorophenyl)sulfonyl)-4-methyoxy-1H-pyrrol-3-yl)-N-methylmethanamine;
9) 1-(5-(2,4-difluorophenyl)-1-((3-(trifluoromethyl)phenyl)sulfonyl)-4-methoxy-1H-pyrrol-3-yl)-N-methylmethanamine;

10) 1-(5-(2,4-difluorophenyl)-1-((3-methylphenyl)sulfonyl)-4-methoxy-1H-pyrrol-3-yl)-N-methylmethanamine;
11) 1-(5-(2,4-difluorophenyl)-1-((3-methoxyphenyl)sulfonyl)-4-methoxy-1H-pyrrol-3-yl)-N-methylmethanamine;
12) 1-(5-(2,4-difluorophenyl)-1-((3-difluoromethoxyphenyl)sulfonyl)-4-methoxy-1H-pyrrol-3-yl)-N-methylmethanamine;
13) 1-(5-(2,6-difluorophenyl)-1-((3-fluorophenyl)sulfonyl)-4-methoxy-1H-pyrrol-3-yl)-N-methylmethanamine;
14) 1-(5-(2,6-difluorophenyl)-1-((3-chlorophenyl)sulfonyl)-4-methoxy-1H-pyrrol-3-yl)-N-methylmethanamine;
15) 1-(5-(2,6-difluorophenyl)-1-((3-(trifluoromethyl)phenyl)sulfonyl)-4-methoxy-1H-pyrrol-3-yl)-N-methylmethanamine;
16) 1-(5-(2,6-difluorophenyl)-1-((3-methylphenyl)sulfonyl)-4-methoxy-1H-pyrrol-3-yl)-N-methylmethanamine;
17) 1-(5-(2,6-difluorophenyl)-1-((3-methoxyphenyl)sulfonyl)-4-methoxy-1H-pyrrol-3-yl)-N-methylmethanamine;
18) 1-(5-(2,6-difluorophenyl)-1-((3-chloro-4-fluorophenyl)sulfonyl)-4-methoxy-1H-pyrrol-3-yl)-N-methylmethanamine;
19) 1-(5-(2,6-difluorophenyl)-1-((3,4-difluorophenyl)sulfonyl)-4-methoxy-1H-pyrrol-3-yl)-N-methylmethanamine;
20) 1-(5-(2-fluoro-6-chlorophenyl)-1-((3-fluorophenyl)sulfonyl)-4-methoxy-1H-pyrrol-3-yl)-N-methylmethanamine;
21) 1-(5-(2-fluoro-6-chlorophenyl)-1-((3-chlorophenyl)sulfonyl)-4-methoxy-1H-pyrrol-3-yl)-N-methylmethanamine;
22) 1-(1-((3-fluorophenyl)sulfonyl)-4-methoxy-5-(2,4,6-trifluorophenyl)-1H-pyrrol-3-yl)-N-methylmethanamine;
23) 1-(1-((3-chlorophenyl)sulfonyl)-4-methoxy-5-(2,4,6-trifluorophenyl)-1H-pyrrol-3-yl)-N-methylmethanamine;
24) 1-(1-((3-trifluoromethylphenyl)sulfonyl)-4-methoxy-5-(2,4,6-trifluorophenyl)-1H-pyrrol-3-yl)-N-methylmethanamine;
25) 1-(1-((3-methoxyphenyl)sulfonyl)-4-methoxy-5-(2,4,6-trifluorophenyl)-1H-pyrrol-3-yl)-N-methylmethanamine;
26) 1-(1-((3,4-difluorophenyl)sulfonyl)-4-methoxy-5-(2,4,6-trifluorophenyl)-1H-pyrrol-3-yl)-N-methanamine;
27) 1-(1-((3-fluorophenyl)sulfonyl)-4-methoxy-5-(2,3,6-trifluorophenyl)-1H-pyrrol-3-yl)-N-methylmethanamine;
28) 1-(1-((3-chlorophenyl)sulfonyl)-4-methoxy-5-(2,3,6-trifluorophenyl)-1H-pyrrol-3-yl)-N-methylmethanamine;
29) 1-(1-((3-trifluoromethylphenyl)sulfonyl)-4-methoxy-5-(2,3,6-trifluorophenyl)-1H-pyrrol-3-yl)-N-methylmethanamine;
30) 1-(1-((3-methoxyphenyl)sulfonyl)-4-methoxy-5-(2,3,6-trifluorophenyl)-1H-pyrrol-3-yl)-N-methylmethanamine;
31) 1-(5-(2,5-difluorophenyl)-1-((3-fluorophenyl)sulfonyl)-4-methoxy-1H-pyrrol-3-yl)-N-methylmethanamine;
32) 1-(5-(2,5-difluorophenyl)-1-((3-trifluoromethylphenyl)sulfonyl)-4-methoxy-1H-pyrrol-3-yl)-N-methylmethanamine; and
33) 1-(5-(2,5-difluorophenyl)-1-((3-methoxyphenyl)sulfonyl)-4-methoxy-1H-pyrrol-3-yl)-N-methylmethanamine.

The compound represented by Chemical Formula 1 or a salt thereof may have a substituent group containing an asymmetric atom. In this case, the compound of Chemical Formula 1 or a salt thereof may be present as an optical isomer such as (R), (S), or racemate (RS). Therefore, unless otherwise specified, the compound of Chemical Formula 1 or a salt thereof includes all optical isomers such as (R), (S), or racemate (RS).

The compound represented by Chemical Formula 1 may be in the form of a pharmaceutically acceptable salt. The salt includes conventional acid addition salts, for example, salts derived from inorganic acids such as hydrochloric acid, hydrobromic acid, sulfuric acid, sulfamic acid, phosphoric acid, or nitric acid, and salts derived from organic acids such as acetic acid, propionic acid, succinic acid, glycolic acid, stearic acid, maleic acid, hydroxy maleic acid, phenylacetic acid, glutamic acid, benzoic acid, salicylic acid, sulfanilic acid, 2-acetoxy-benzoic acid, fumaric acid, toluenesulfonic acid, methanedisulfonic acid, ethanedisulfonic acid, oxalic acid, or trifluoroacetic acid. Preferably, the salt may be hydrochloride or fumarate salt.

As an example, the compound represented by Chemical Formula 1 may be prepared by the method as shown in the following Reaction Scheme 1:

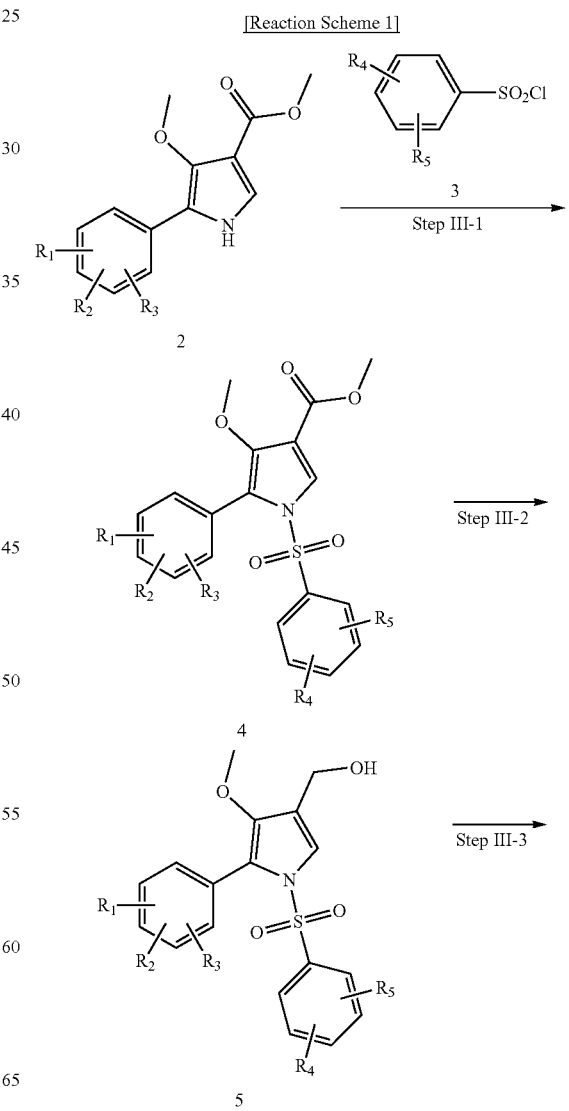

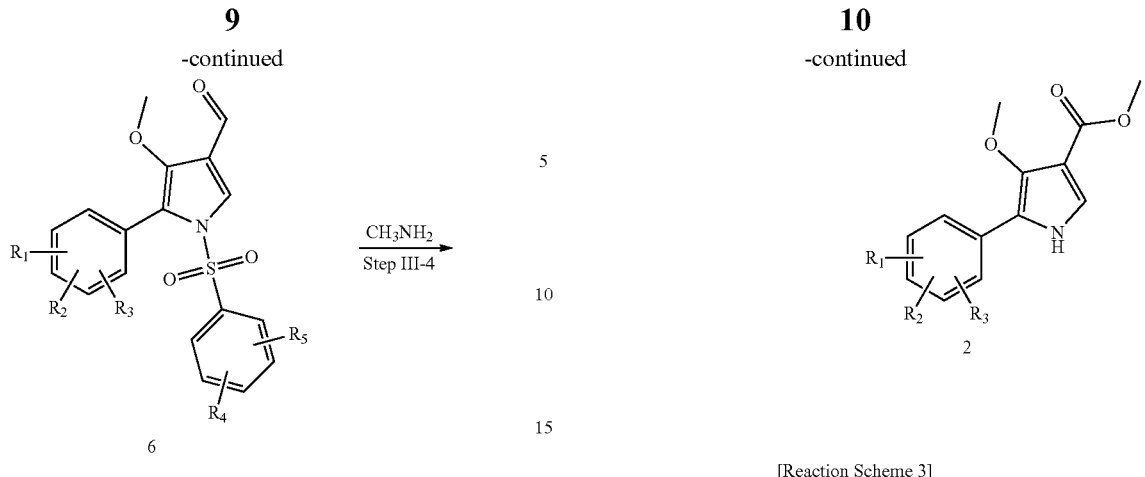
in Reaction Scheme 1, $R_1$ to $R_5$ are as defined above.
Also, the compound represented by Chemical Formula 2 in Reaction Scheme 1 may be prepared by the method as shown in the following Reaction Scheme 2 or 3:
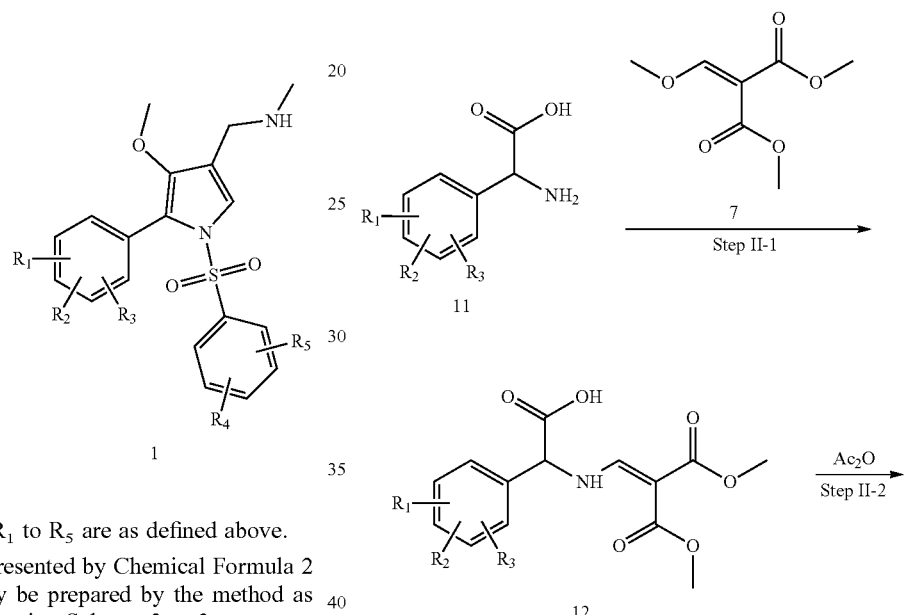
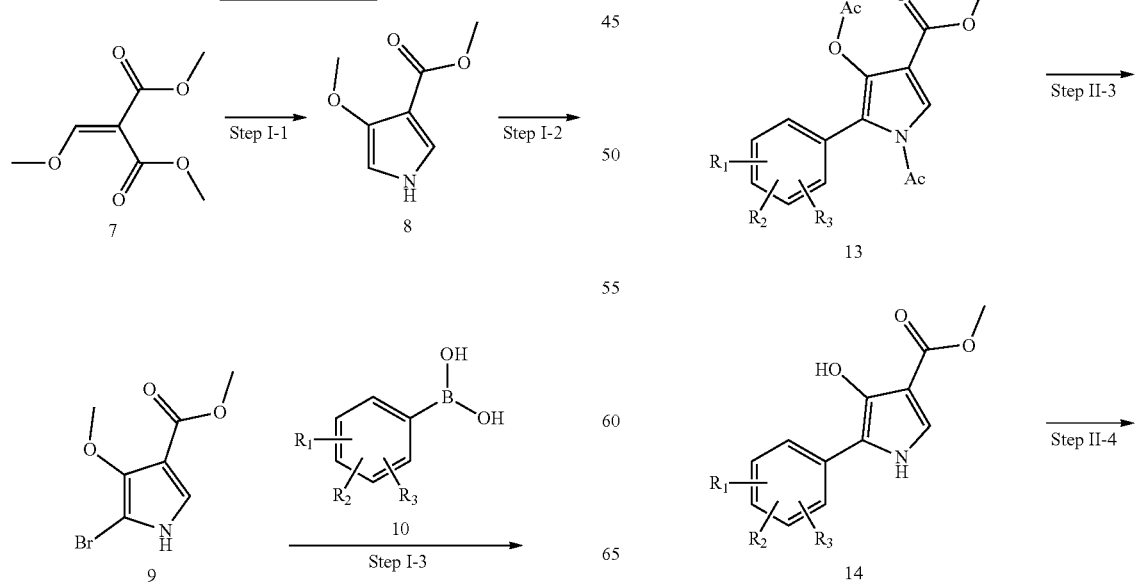

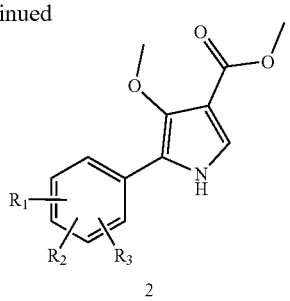

2 in Reaction Schemes 2 and 3, $R_1$ to $R_3$ are as defined above, and 'Ac' means acetyl.

First, the method represented by Reaction Scheme 2 which can prepare the compounds of Chemical Formula 2 can be carried out via Steps I-1 to I-3.

The Step I-1 is a step of reacting dimethyl 2-(methoxymethylene)malonate represented by Chemical Formula 7 with tosylmethyl isocyanate to prepare a compound represented by Chemical Formula 8, which is a step of cyclization reaction of pyrrole. The reaction may be carried out in an organic solvent such as acetonitrile.

The Step I-2 is a step of brominating the compound represented by Chemical Formula 8 to prepare a compound represented by Chemical Formula 9. The bromination can be carried out by using a reagent such as N-bromosuccinimide (NBS) which can introduce bromine at the position of hydrogen of pyrrole in the compound represented by Chemical Formula 8. Further, the reaction can be carried out in an organic solvent such as tetrahydrofuran.

The Step I-3 is a step of reacting the compound represented by Chemical Formula 9 with the compound represented by Chemical Formula 10 in the presence of a metal catalyst to prepare a compound represented by Chemical Formula 2. As the metal catalyst, a conventional palladium (Pd) catalyst can be used. Non-limiting examples thereof may include $Pd(PPh_3)_4$, $Pd(OAc)_2$, $PdCl_2$, $PdCl_2(PPh_3)_4$, $PdBr_2$, $Pd(acac)_2$, $Pd_2(dba)_3$, $Pd(dba)_2$ and the like. Here, 'Ph' means phenyl, 'acac' means acetylacetonate, and 'dba' means dibenzylideneacetone. In addition, the reaction may be carried out in a polar solvent such as methanol, ethanol, tert-butanol, acetone, dimethylformamide, acetonitrile, or water.

Alternatively, the compounds of Chemical Formula 2 can be prepared by Reaction Scheme 3, and the method represented by Reaction Scheme 3 can be carried out via Steps II-1 to II-4.

The Step II-1 is a step of reacting the compound represented by Chemical Formula 11 with dimethyl 2-(methoxymethylene)malonate represented by Chemical Formula 7 to prepare a compound represented by Chemical Formula 12. The reaction can be carried out in an alcohol solvent such as methanol, ethanol, or tert-butanol for 1 to 4 hours.

The Step II-2 is a step of reacting the compound represented by Chemical Formula 12 with acetic anhydride ($Ac_2O$) to prepare a compound represented by Chemical Formula 13, which is a step of cyclization reaction of pyrrole. The reaction may be carried out in the presence of a base such as triethylamine for 1 to 2 hours.

The Step II-3 is a step of hydrolyzing the compound represented by Chemical Formula 13 to prepare a compound represented by Chemical Formula 14. Through the Step, a hydroxy group can be introduced in pyrrole. Further, the hydrolysis can be carried out by using a base such as sodium hydroxide for 10 minutes to 30 minutes.

The Step II-4 is a step of methylating the compound represented by Chemical Formula 14 to prepare a compound represented by Chemical Formula 2. The methylation can be carried out by using a methylating agent such as trimethylsilyl diazomethane (TMS-$CH_2N_2$), or by reacting with dimethyl sulfate in the presence of sodium hydroxide. Further, the reaction can be carried out in an organic solvent such as dimethylformamide, or diethyl ether for 1 to 48 hours.

Then, the compound represented by Chemical Formula 1 can be prepared in accordance with Reaction Scheme 1. The method represented by Reaction Scheme 1 may be carried out via Steps III-1 to III-4.

The Step III-1 is a step of reacting the compound represented by Chemical Formula 2 with the compound represented by Chemical Formula 3 to prepare a compound represented by Chemical Formula 4, which is a step of introducing a substituted phenylsulfonyl group in pyrrole of the compound represented by Chemical Formula 2. The reaction is carried out in an organic solvent such as dimethylformamide in the presence of sodium hydride for 20 to 30 minutes.

The Step III-2 is a step of reducing the compound represented by Chemical Formula 4 to prepare a compound represented by Chemical Formula 5. The reduction can be carried out in an organic solvent such as tetrahydrofuran using a reducing agent such as diisobutyl aluminum hydride (DIBAL).

The Step III-3 is a step of oxidizing the compound represented by Chemical Formula 5 to prepare a compound represented by Chemical Formula 6. The oxidation of an alcohol group of the compound represented by Chemical Formula 5 can be carried out in an organic solvent such as dichloromethane using an oxidizing agent such as pyridinium chlorochromate (PCC) for 30 minutes to 2 hours.

The Step III-4 is a step of reacting the compound represented by Chemical Formula 6 with methylamine to prepare a compound represented by Chemical Formula 1, which is a step of reductive amination. The reductive amination can be carried out in an organic solvent such as tetrahydrofuran using a reducing agent such as sodium borohydride for 30 minutes to 1 hour.

If necessary, the pharmaceutically acceptable acid addition salts such as hydrochloride or fumarate can be prepared by adding an acid such as hydrochloric acid or fumaric acid to the compound represented by Chemical Formula 1 prepared as described above. For example, the compound represented by Chemical Formula 1 can be reacted with an acid solution in an organic solvent such as dichloromethane for 1 to 2 hours to prepare an acid addition salt.

On the other hand, the present invention provides a pharmaceutical composition for the prevention and treatment of gastrointestinal damage due to gastrointestinal tract ulcer, gastritis, reflux esophagitis or *H. pylori*, comprising the compounds represented by Chemical Formula 1 or pharmaceutically acceptable salts thereof.

Also, the present invention provides a pharmaceutical composition for the prevention and treatment of 5-HT receptor-mediated or muscarinic acetylcholine receptor-mediated diseases, comprising the compounds represented by Chemical Formula 1 or pharmaceutically acceptable salts thereof. In this case, the 5-HT receptor-mediated or muscarinic acetylcholine receptor-mediated diseases may be depression, manic depression, schizophrenia, autism, obsessive-compulsive neurosis, anxiety disorder, migraine, hypertension, eating disorder, irritable bowel syndrome (IBS), peptic ulcer, diabetic neuropathy, asthma, and overactive bladder.

The pharmaceutical composition may comprise pharmaceutically acceptable carriers that are commonly used, such as excipients, disintegrants, sweetening agents, lubricants or flavoring agents. The pharmaceutical composition can be formulated into preparations for oral administration such as tablets, capsules, powders, granules, suspensions, emulsions or syrups; or preparations for parenteral administration such as injections in accordance with conventional methods. The preparations can be formulated into various forms, for example, in a single dosage form or multiple dosage forms.

The composition may be administered orally, or administered parenterally, including intravenous, intramuscular, intraperitoneal, subcutaneous, rectal and local routes of administration. The composition may be preferably administered orally. Therefore, the composition may be formulated into various forms such as tablets, capsules, aqueous solutions or suspensions. In the case of tablets for oral administration, carriers such as lactose or corn starch and lubricants such as magnesium stearate can be commonly added. In the case of capsules for oral administration, lactose and/or dried corn starch can be used as a diluent. When an aqueous suspension is required for oral use, the active ingredient may be combined with emulsions and/or suspensions. If necessary, certain sweetening and/or flavoring agents can be added. For intramuscular, intraperitoneal, subcutaneous and intravenous administration, sterile solutions of the active ingredient are usually prepared, and the pH of the solutions should be suitably adjusted and buffered. For intravenous administration, the total concentration of solutes should be controlled in order to render the preparation isotonic. The composition may be in the form of an aqueous solution containing a pharmaceutically acceptable carrier, e.g., saline, at a pH level of 7.4. The solution may be introduced into a patient's intramuscular blood-stream by local bolus injection.

In this case, the pharmaceutical composition may be administered in a therapeutically effective amount. Therefore, the compound represented by Chemical Formula 1 or a pharmaceutically acceptable salt thereof contained in the pharmaceutical composition may be administered in an effective amount ranging from about 0.01 mg/kg to about 100 mg/kg per day to a subject patient. Of course, the dosage may be changed according to the patient's age, weight, susceptibility, symptom or the efficacy of the compound.

Below, the present invention is described by way of examples and experimental examples. These examples are provided for illustration purpose only, and are not intended to limit the scope of the invention.

The analysis of the compounds prepared in Examples below was carried out as follows: Nuclear Magnetic Resonance (NMR) spectrum analysis was performed on Bruker 400 MHz spectrometer, a chemical shift was analyzed in ppm, a column chromatography was performed on silica gel (Merck, 70-230 mesh) (W. C. Still, J. Org. Chem., (43), 2923, 1978). And also, the starting materials in each example were synthesized from the known compounds, or were purchased from Sigma Aldrich.

Example 2: Preparation of 1-(5-(2-fluorophenyl)-4-methoxy-1-((3-(trifluoromethyl)phenyl)sulfonyl)-1H-pyrrol-3-yl)-N-methylamine hydrochloride

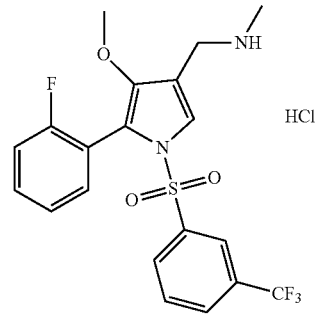 [SMILES: CNCc1cn(S(=O)(=O)c2cccc(C(F)(F)F)c2)c(-c2ccccc2F)c1OC ; Cl]

(Step 2-1) Preparation of 2-(2-fluorophenyl)-2-((3-methoxy-2-(methoxycarbonyl)-3-oxoprop-1-en-1-yl)amino)acetic acid 2-Fluorophenyl glycine (200.0 g, 1.18 mol), dimethyl 2-(methoxymethylene)malonate (187.2 g, 1.07 mol), and sodium acetate (97.0 g, 1.18 mol) were added to methanol (1000.0 ml), and the mixture was then refluxed at 60° C. for 4 hours. The reaction mixture was cooled to room temperature, and then filtered. The filtrate was concentrated under reduced pressure. To the resulting residue, water (140.0 ml) and 1N HCl aqueous solution (561.0 ml) were added, and then filtered. The resulting solid was dried under reduced pressure to give 301.0 g of the title compound. (Yield: 81.8%).

$^1$H-NMR (500 MHz, CDCl$_3$): 9.97 (q, 1H), 8.1 (d, 1H), 7.46-7.40 (m, 2H), 7.25 (t, 1H), 7.20 (t, 1H), 5.57 (d, 1H), 3.75 (s, 3H), 3.64 (s, 3H)

(Step 2-2) Preparation of methyl 4-acetoxy-1-acetyl-5-(2-fluorophenyl)-1H-pyrrol-3-carboxylate Acetic anhydride (1440.0 ml), molecular sieves (4A, 96.0 g) and triethylamine (960.0 ml) were added to 2-(2-fluorophenyl)-2-((3-methoxy-2-(methoxycarbonyl)-3-oxoprop-1-en-1-yl)amino)acetic acid (301.0 g, 0.96 mol) prepared in Step 2-1. The reaction mixture was refluxed at 140° C. for 1 hour and then cooled to 0° C. To the reaction mixture, ice water (2425.0 ml) was added at 0° C., stirred at room temperature for 1 hour, and then extracted with ethyl acetate. The extract was dried over anhydrous magnesium sulfate, and concentrated under reduced pressure. The resulting residue was purified by silica gel column chromatography (ethyl acetate:n-hexane=1:3 (v/v)) to give 48.8 g of the title compound. (Yield: 15.1%).

$^1$H-NMR (500 MHz, CDCl$_3$): 7.87 (s, 1H), 7.40-7.38 (q, 1H), 7.30-7.26 (q, 1H), 7.18 (t, 1H), 7.11 (t, 1H), 3.83 (s, 3H), 2.16 (s, 3H), 2.21 (s, 3H)

(Step 2-3) Preparation of methyl 5-(2-fluorophenyl)-4-hydroxy-1H-pyrrol-3-carboxylate Tetrahydrofuran (130.0 ml) and water (32.5 ml) were added to methyl 4-acetoxy-1-acetyl-5-(2-fluorophenyl)-1H-pyrrol-3-carboxylate (48.8 g, 152.8 mmol) prepared in Step 2-2. The reaction mixture was cooled to 0° C., to which sodium hydroxide (11.7 g, 305.6 mol) was added and then stirred at 0° C. for 10 minutes. The reaction mixture was neutralized using 1N hydrochloric acid aqueous solution and then extracted with ethyl acetate. The extract was dried over anhydrous magnesium sulfate, and concentrated under reduced pressure. The resulting residue was purified by silica gel column chromatography (ethyl acetate:n-hexane=1:4 (v/v)) to give 30.5 g of the title compound. (Yield: 89.05%)

$^1$H-NMR (500 MHz, CDCl$_3$): 8.92 (s, 1H), 8.20-8.16 (m, 2H), 7.20 (t, 1H), 7.14-7.06 (m, 3H), 3.87 (s, 3H)

(Step 2-4) Preparation of methyl 5-(2-fluorophenyl)-4-methoxy-1H-pyrrol-3-carboxylate Methyl 5-(2-fluorophenyl)-4-hydroxy-1H-pyrrol-3-carboxylate (30.3 g, 128.7 mmol) prepared in Step 2-3 was dissolved in dimethylformamide (150.0 ml). To the resulting solution, sodium hydride (60%, dispersion in liquid paraffin) (5.2 g, 128.7 mmol) was added at 0° C., and then stirred at 0° C. for 30 minutes. Dimethyl sulfate (12.2 ml, 128.7 mmol) was added to the reaction mixture, and then stirred at 0° C. for 1 hour. Water was added to the reaction mixture and extracted with ethyl acetate. The extract was dried over anhydrous magnesium sulfate, and then concentrated under reduced pressure. The resulting residue was purified by silica gel column chromatography (ethyl acetate:n-hexane=1:4 (v/v)) to give 22.8 g of the title compound. (Yield: 71.0%)

$^1$H-NMR (500 MHz, CDCl$_3$): 8.91 (s, 1H), 8.17-8.15 (m, 1H), 7.32 (d, 1H), 7.22-7.17 (m, 2H), 7.14-7.09 (m, 1H), 3.89 (s, 3H), 3.86 (s, 3H)

(Step 2-5) Preparation of methyl 5-(2-fluorophenyl)-4-methoxy-1-((3-(trifluoromethyl)phenyl)sulfonyl)-1H-pyrrol-3-carboxylate Methyl 5-(2-fluorophenyl)-4-methoxy-1H-pyrrol-3-carboxylate (22.47 g, 90.0 mmol) prepared in Step 2-4 was dissolved in dimethylformamide (113.0 ml). To the resulting solution, sodium hydride (60%, dispersion in liquid paraffin) (4.35 g, 108.2 mmol) was added at 0° C., and then stirred at 0° C. for 20 minutes. 3-(trifluoromethyl)benzenesulfonyl chloride (28.77 g, 108.2 mmol) was added to the reaction mixture and stirred at room temperature for 30 minutes. Water was added to the reaction mixture and extracted with ethyl acetate. The extract was dried over anhydrous magnesium sulfate, and then concentrated under reduced pressure. The resulting residue was purified by silica gel column chromatography (ethyl acetate:n-hexane=1:4 (v/v)) to give 28.04 g of the title compound. (Yield: 92.2%)

$^1$H-NMR (500 MHz, CDCl$_3$): 8.01 (s, 1H), 7.84 (d, 1H), 7.66 (d, 1H), 7.58 (t, 1H), 7.53 (s, 1H), 7.44-7.42 (m, 1H), 7.17-7.15 (m, 2H), 6.96 (t, 1H), 3.87 (s, 3H), 3.59 (s, 3H)

(Step 2-6) Preparation of (5-(2-fluorophenyl)-4-methoxy-1-((3-(trifluoromethyl)phenyl)sulfonyl)-1H-pyrrol-3-yl)methanol Methyl 5-(2-Fluorophenyl)-4-methoxy-1-((3-(trifluoromethyl)phenyl)sulfonyl)-1H-pyrrol-3-carboxylate (27.7 g, 60.8 mmol) prepared in Step 2-5 was dissolved in tetrahydrofuran (140.0 ml). To the resulting solution, diisopropylbutyl aluminum hydride (1.0 M tetrahydrofuran solution) (182 ml, 182.2 mmol) was added at 0° C. and then stirred at room temperature for 1 hour. Water was added to the reaction mixture at 0° C. and then extracted with ethyl acetate. The extract was dried over anhydrous magnesium sulfate, and then concentrated under reduced pressure. The resulting residue was purified by silica gel column chromatography (ethyl acetate:n-hexane=1:4 (v/v)) to give 21.55 g of the title compound. (Yield: 82.6%)

$^1$H-NMR (500 MHz, CDCl$_3$): 7.80 (d, 1H), 7.66 (d, 1H), 7.57-7.54 (m, 2H), 7.40 (q, 1H), 7.36 (s, 1H), 7.19-7.12 (m, 2H), 6.98 (t, 1H), 4.57 (d, 2H), 3.46 (s, 3H)

(Step 2-7) Preparation of 5-(2-fluorophenyl)-4-methoxy-1-((3-(trifluoromethyl)phenyl)sulfonyl)-1H-pyrrol-3-carbaldehyde (5-(2-fluorophenyl)-4-methoxy-1-((3-(trifluoromethyl)phenyl)sulfonyl)-1H-pyrrol-3-yl)methanol (21.4 g, 50.0 mmol) prepared in Step 2-6 was dissolved in dichloromethane (214.0 ml). To the resulting solution, pyridinium chlorochromate (32.4 g, 150.0 mmol) was added, stirred at room temperature for 30 minutes, and then filtered through celite pad (32.4 g). The filtrate was concentrated under reduced pressure. The resulting residue was purified by silica gel column chromatography (ethyl acetate:n-hexane=1:2 (v/v)) to give 15.1 g of the title compound. (Yield: 70.7%)

$^1$H-NMR (500 MHz, CDCl$_3$): 9.91 (s, 1H), 8.02 (s, 1H), 7.86 (d, 1H), 7.66 (d, 1H), 7.59 (t, 1H), 7.47-7.42 (m, 1H), 7.21-7.15 (m, 2H), 6.95 (t, 1H), 3.60 (s, 3H)

(Step 2-8) Preparation of 1-(5-(2-fluorophenyl)-4-methoxy-1-((3-(trifluoromethyl)phenyl)sulfonyl)-1H-pyrrol-3-yl)-N-methylmethanamine 5-(2-fluorophenyl)-4-methoxy-1-((3-(trifluoromethyl)phenyl)sulfonyl)-1H-pyrrol-3-carbaldehyde (14.9 g, 34.9 mmol) prepared in Step 2-7 was dissolved in tetrahydrofuran (74.5 ml). Methylamine (2.0 M tetrahydrofuran solution) (174.2 ml, 348.4 mmol) was added to the resulting solution and stirred at room temperature for 30 minutes. Sodium borohydride (5.27 g, 139.3 mmol) was added to the reaction mixture, stirred at room temperature for 30 minutes, neutralized using 1N hydrochloric acid aqueous solution, and then extracted with ethyl acetate. The extract was dried over anhydrous magnesium sulfate, and then concentrated under reduced pressure. The resulting residue was purified by silica gel column chromatography (ethyl acetate:n-hexane=1:2 (v/v)) to give 9.2 g of the title compound. (Yield: 70.7%)

$^1$H-NMR (500 MHz, MeOD): 8.01 (s, 1H), 7.78-7.72 (m, 3H), 7.55-7.50 (m, 2H), 7.19 (t, 1H), 7.14 (t, 1H), 7.03 (t, 1H), 4.07 (s, 2H), 3.42 (s, 3H), 2.70 (s, 3H)

(Step 2-9) Preparation of 1-(5-(2-fluorophenyl)-4-methoxy-1-((3-(trifluoromethyl)phenyl)sulfonyl)-1H-pyrrol-3-yl)-N-methylmethanamine hydrochloride 1-(5-(2-fluorophenyl)-4-methoxy-1-((3-(trifluoromethyl)phenyl)sulfonyl)-1H-pyrrol-3-yl)-N-methylmethanamine (9.2 g, 20.8 mmol) prepared in Step 2-8 was dissolved in dichloromethane (18.4 ml). Hydrochloric acid solution (2.0M diethyl ether solution) (21.8 ml, 43.6 mmol) was added to the resulting solution, stirred at 0° C. for 1 hour and then filtered. The resulting solid was dried under reduced pressure to give 9.48 g of the title compound. (Yield: 88.5%)

Molecular weight: 478.89

$^1$H-NMR (500 MHz, MeOD): 8.00 (d, 1H), 7.77-7.71 (m, 2H), 7.68 (s, 1H), 7.55 (s, 1H), 7.50 (q, 1H), 7.18 (t, 1H), 7.71 (t, 1H), 7.03 (t, 1H), 4.02 (s, 2H), 3.42 (s, 3H), 2.67 (s, 3H)

Example 8: Preparation of 1-(5-(2,4-difluorophenyl)-1-((3-fluorophenyl)sulfonyl)-4-methoxy-1H-pyrrol-3-yl)-N-methylmethanamine hydrochloride

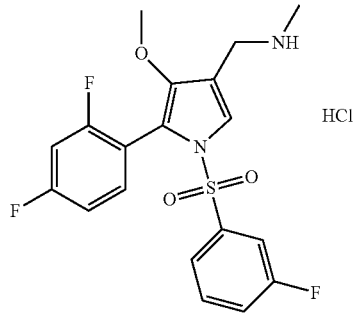 [SMILES: CNCc1cn(S(=O)(=O)c2cccc(F)c2)c(-c2ccc(F)cc2F)c1OC ; Cl]

(Step 8-1) Preparation of 2-(2,4-difluorophenyl)-2-((3-methoxy-2-(methoxycarbonyl)-3-oxoprop-1-en-1-yl)amino)acetic acid 2,4-Difluorophenyl glycine (150.0 g, 801.5 mmol), dimethyl 2-(methoxymethylene)malonate (126.9 g, 728.6 mmol), and sodium acetate (65.8 g, 801.5 mmol) were added to methanol (800.0 ml), and then refluxed at 60° C. for 4 hours. The reaction mixture was cooled to room temperature, and concentrated under reduced pressure to remove about 70% of methanol, and then filtered. The resulting solid was dried reduced pressure to give 190.0 g of the title compound. (Yield: 79.2%)

$^1$H-NMR (500 MHz, CDCl$_3$): 8.02-7.99 (m, 1H), 7.45-7.40 (m, 1H), 7.00-6.95 (m, 2H), 5.16 (s, 1H), 3.74 (s, 3H), 3.76 (s, 3H)

(Step 8-2) Preparation of methyl 5-(2,4-difluorophenyl)-4-hydroxy-1H-pyrrol-3-carboxylate Acetic anhydride (1731.2 ml) and triethylamine (577.1 ml) were added to 2-(2,4-difluorophenyl)-2-((3-methoxy-2-(methoxycarbonyl)-3-oxoprop-1-en-1-yl)amino)acetic acid (190.0 g, 577.1 mmol) prepared in Step 8-1. The reaction mixture was refluxed at 140° C. for 30 minutes and then cooled to 0° C. To the reaction mixture, ice water (577.1 ml) was added at 0° C., stirred at room temperature for 1 hour and then extracted with ethyl acetate. The extract was dried over anhydrous magnesium sulfate and then concentrated under reduced pressure. The resulting compound was filtered using a silica gel to remove a solid, and then concentrated under reduced pressure.

Tetrahydrofuran (140.0 ml) and water (120.0 ml) were added to the resulting residue, cooled to 0° C., followed by addition of sodium hydroxide (46.17 g, 1154.2 mmol). The reaction mixture was stirred at 0° C. for 30 minutes, neutralized using 1N hydrochloric acid aqueous solution and then extracted with ethyl acetate. The extract was dried over anhydrous magnesium sulfate, and then concentrated under reduced pressure. The resulting residue was purified by silica gel column chromatography (ethyl acetate:n-hexane=1:4 (v/v)) to give 22.0 g of the title compound. (Yield: 15.1%)

$^1$H-NMR (500 MHz, CDCl$_3$): 8.80 (s, 1H), 8.17-8.12 (m, 2H), 7.13 (d, 1H), 6.95 (t, 1H), 6.86-6.83 (m, 1H), 3.88 (s, 3H)

(Step 8-3) Preparation of Methyl 5-(2,4-difluorophenyl)-4-methoxy-1H-pyrrol-3-carboxylate Methyl 5-(2,4-difluorophenyl)-4-hydroxy-1H-pyrrol-3-carboxylate (22.0 g, 86.9 mmol) prepared in Step 8-2 was dissolved in tetrahydrofuran (434.5 ml) and methanol (173.9 ml). (Trimethylsilyl)diazomethane (2.0M diethyl ether solution, 173.8 ml) was added to the reaction mixture and then stirred at room temperature for 48 hours. Water was added to the reaction mixture, and extracted with ethyl acetate. The extract was dried over anhydrous magnesium sulfate, and then concentrated under reduced pressure. The resulting residue was purified by silica gel column chromatography (ethyl acetate:n-hexane=1:4 (v/v)) to give 18.1 g of the title compound. (Yield: 75.3%)

$^1$H-NMR (500 MHz, CDCl$_3$): 8.78 (s, 1H), 8.12 (m, 1H), 7.30 (d, 1H), 6.95 (t, 1H), 6.88 (t, 1H), 3.87 (s, 3H), 3.85 (s, 3H)

(Step 8-4) Preparation of methyl 5-(2,4-difluorophenyl)-4-methoxy-1-((3-fluorophenyl)sulfonyl)-1H-pyrrol-3-carboxylate Methyl 5-(2,4-difluorophenyl)-4-methoxy-1H-pyrrol-3-carboxylate (18.0 g, 67.4 mmol) prepared in Step 8-3 was dissolved in dimethylformamide (335.0 ml). Sodium hydride (60% dispersion in liquid paraffin) (4.0 g, 101.0 mmol) was added to the resulting solution at room temperature, and stirred at room temperature for 10 minutes. 3-Fluoro-benzenesulfonyl chloride (13.37 ml, 101.0 mmol) was added to the reaction mixture and stirred at room temperature for 1 hour. Water was added to the reaction mixture and extracted with ethyl acetate. The extract was dried over anhydrous magnesium sulfate, and then concentrated under reduced pressure. The resulting residue was purified by silica gel column chromatography (ethyl acetate:n-hexane=1:4 (v/v)) to give 26.1 g of the title compound. (Yield: 91.1%)

$^1$H-NMR (500 MHz, CDCl$_3$): 7.98 (s, 1H), 7.43-7.39 (m, 1H), 7.30 (t, 1H), 7.23 (d, 1H), 7.15 (q, 1H), 7.67 (q, 1H), 6.91 (t, 1H), 6.77 (t, 1H), 3.87 (s, 3H), 3.61 (s, 3H)

(Step 8-5) Preparation of 5-(2,4-difluorophenyl)-4-methoxy-1-((3-fluorophenyl)sulfonyl)-1H-pyrrol-3-carbaldehyde Methyl 5-(2,4-difluorophenyl)-4-methoxy-1-((3-fluorophenyl)sulfonyl)-1H-pyrrol-3-carboxylate (26.0 g, 61.1 mmol) prepared in Step 8-4 was dissolved in tetrahydrofuran (300.0 ml). Diisobutylaluminium hydride (1.0M tetrahydrofuran solution) (183.4 ml, 183.4 mmol) was added to the resulting solution at 0° C., stirred at room temperature for 1 hour, neutralized using 1N hydrochloric acid solution, and then extracted with ethyl acetate. The extract was dried over anhydrous magnesium sulfate and then concentrated under reduced pressure.

The resulting residue was dissolved in dichloromethane (300.0 ml) to which celite (26.0 g) and pyridinium chlorochromate (39.5 g, 183.4 mmol) were added. The reaction mixture was stirred at room temperature for 1 hour and then filtered to remove a solid. The filtrate was concentrated under reduced pressure. The resulting residue was purified by silica gel column chromatography (ethyl acetate:n-hexane=1:2 (v/v)) to give 17.2 g of the title compound. (Yield: 70.9%)

¹H-NMR (500 MHz, CDCl₃): 9.89 (s, 1H), 7.99 (s, 1H), 7.45-7.41 (m, 1H), 7.33 (s, 1H), 7.25 (d, 1H), 7.18 (q, 1H), 7.05 (s, 1H), 6.92 (t, 1H), 6.77 (t, 1H), 3.63 (s, 3H)

(Step 8-6) 1-(5-(2,4-difluorophenyl)-4-methoxy-1-((3-fluorophenyl)sulfonyl)-1H-pyrrol-3-yl)-N-methylmethanamine 5-(2,4-difluorophenyl)-4-methoxy-1-((3-fluorophenyl)sulfonyl)-1H-pyrrol-3-carbaldehyde (17.0 g, 43.0 mmol) prepared in Step 8-5 was dissolved in methanol (430.0 ml). Methyl amine (9.8M ethanol solution) (87.8 ml, 860.0 mmol) was added to the resulting solution and then stirred at room temperature for 30 minutes. Sodium borohydride (16.3 g, 430.0 mmol) was added to the reaction mixture and stirred at room temperature for 30 minutes. Water was added to the reaction mixture and then extracted with ethyl acetate. The resulting extract was dried over anhydrous magnesium sulfate, and then concentrated under reduced pressure. The resulting residue was purified by silica gel column chromatography (ethyl acetate:n-hexane=1:2 (v/v)) to give 15.2 g of the title compound. (Yield: 86.1%)

¹H-NMR (500 MHz, CDCl₃): 7.39-7.35 (m, 1H), 7.26-7.20 (m, 2H), 7.15 (q, 1H), 7.06 (d, 1H), 6.87 (t, 1H), 6.78 (t, 1H), 3.60 (d, 2H), 3.44 (s, 3H), 2.45 (s, 3H)

(Step 8-7) Preparation of 1-(5-(2,4-difluorophenyl)-1-((3-fluorophenyl)sulfonyl)-4-methoxy-1H-pyrrol-3-yl)-N-methylmethane hydrochloride 1-(5-(2,4-difluorophenyl)-4-methoxy-1-((3-fluorophenyl)sulfonyl)-1H-pyrrol-3-yl)-N-methylmethanamine (15.0 g, 36.6 mmol) prepared in Step 8-6 was dissolved in ethylacetate (36.6 ml) and then hydrochloric acid solution (2.0 M diethylether solvent) (36.6 ml, 73.1 mmol) was added thereto. The reaction mixture was stirred at room temperature for 1 hour and then filtered. The resulting solid was dried under reduced pressure to give 15.1 g of the title compound. (Yield: 92.5%).

Molecular weight: 446.87

¹H-NMR (500 MHz, MeOD): 7.69 (s, 1H), 7.58-7.53 (m, 1H), 7.45 (t, 1H), 7.30 (d, 1H), 7.20-7.15 (m, 2H), 7.02-6.94 (m, 2H), 4.07 (d, 2H), 3.46 (s, 3H), 2.71 (s, 3H)

Example 22: Preparation of 1-(1-((3-fluorophenyl)sulfonyl)-4-methoxy-5-(2,4,6-trifluorophenyl)-1H-pyrrol-3-yl)-N-methylmethanamine hydrochloride

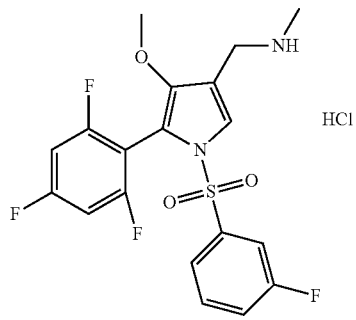 [SMILES: CNCc1cn(S(=O)(=O)c2cccc(F)c2)c(-c2c(F)cc(F)cc2F)c1OC ; Cl]

(Step 22-1) Preparation of methyl 4-acetoxy-1-acetyl-5-(2,4,6-trifluorophenyl)-1H-pyrrol-3-carboxylate Sodium cyanide (16.1 g, 327.9 mmol) and ammonium chloride (17.5 g, 327.9 mmol) were added to water (156 ml) and then stirred at room temperature for 10 minutes. A solution of 2,4,6-trifluorobenzaldehyde (50.0 g, 312.3 mmol) in methanol (156.0 ml) was added to the reaction mixture and then stirred at room temperature for 24 hours. The reaction mixture was concentrated under reduced pressure, and then extracted with dichloromethane. The extract was dried over anhydrous magnesium sulfate, and then concentrated under reduced pressure. 6N hydrochloric acid aqueous solution (312.0 ml) was added to the resulting residue and refluxed at 100° C. for 48 hours. The reaction mixture was cooled to room temperature, and then dried under reduced pressure to give 2,4,6-trifluoro-phenyl glycine.

The obtained 2,4,6-trifluorophenyl glycine, dimethyl-2-(methoxymethylene)malonate (61.5 g, 272.7 mmol) and sodium acetate (24.6 g, 300.0 mmol) were dissolved in methanol (300.0 ml) and then refluxed at 60° C. for 4 hours. The reaction mixture was cooled to 0° C. and then filtered. Acetic anhydride (900.0 ml) and triethylamine (300.0 ml) were added to the filtrate. The reaction mixture was refluxed at 140° C. for 30 minutes and then cooled to 0° C. Ice water (900.0 ml) was added to the reaction mixture at 0° C., stirred at room temperature for one hour and then extracted with ethyl acetate. The extract was dried over anhydrous magnesium sulfate and then concentrated under reduced pressure. The resulting residue was purified by silica gel column chromatography (ethyl acetate:n-hexane=1:4 (v/v)) to give 10.3 g of the title compound. (Yield: 9.3%)

¹H-NMR (500 MHz, CDCl₃): 7.86 (s, 1H), 6.75-6.75 (q, 3H), 3.82 (s, 3H), 2.55 (s, 3H), 2.17 (s, 3H)

(Step 22-2) Preparation of methyl 4-hydroxy-5-(2,4,6-trifluorophenyl)-1H-pyrrol-3-carboxylate Tetrahydrofuran (24.0 ml) and water (6.0 ml) were added to methyl 4-acetoxy-1-acetyl-5-(2,4,6-trifluorophenyl)-1H-pyrrol-3-carboxylate (10.0 g, 28.1 mmol) prepared in Step 22-1. The reaction mixture was cooled to 0° C. to which sodium hydroxide (2.3 g, 56.3 mmol) was added. The reaction mixture was stirred at room temperature for 30 minutes, neutralized using 1N hydrochloric acid aqueous solution and then extracted with ethyl acetate. The extract was dried over anhydrous magnesium sulfate, and then concentrated under reduced pressure. The resulting residue was purified by silica gel column chromatography (ethyl acetate:n-hexane=1:4 (v/v)) to give 4.7 g of the title compound. (Yield: 61.7%)

¹H-NMR (500 MHz, CDCl₃): 8.18 (s, 1H), 7.87 (s, 1H), 7.23 (d, 1H), 6.76 (t, 3H), 3.87 (s, 3H)

(Step 22-3) Preparation of methyl 4-methoxy-5-(2,4,6-trifluorophenyl)-1H-pyrrol-3-carboxylate Methyl 4-hydroxy-5-(2,4,6-trifluorophenyl)-1H-pyrrol-3-carboxylate (4.5 g, 16.6 mmol) prepared in Step 22-2 was added to tetrahydrofuran (83.0 ml) and methanol (33.2 ml). (Trimethylsilyl)diazomethane (2.0M diethyl ether solution) (33.2 ml) was added to the resulting solution and then stirred at room temperature for 48 hours. Water was added to the reaction mixture and then extracted with ethyl acetate. The extract was dried over anhydrous magnesium sulfate, and then concentrated under reduced pressure. The resulting residue was purified by silica gel column chromatography (ethyl acetate:n-hexane=1:4 (v/v)) to give 3.9 g of the title compound. (Yield: 81.3%)

$^1$H-NMR (500 MHz, CDCl$_3$): 8.17 (s, 1H), 7.39 (d, 1H), 6.7 (t, 2H), 3.86 (s, 3H), 3.84 (s, 3H)

(Step 22-4) Preparation of methyl 1-((3-fluorophenyl)sulfonyl)-4-methoxy-5-(2,4,6-trifluorophenyl)-1H-pyrrol-3-carboxylate Methyl 4-methoxy-5-(2,4,6-trifluorophenyl)-1H-pyrrol-3-carboxylate (3.8 g, 13.3 mmol) prepared in Step 22-3 was dissolved in dimethylformamide (150.0 ml). Sodium hydride (60% dispersion in liquid paraffin) (0.78 g, 20.0 mmol) was added to the resulting solution at room temperature, and then stirred at room temperature for 10 minutes. 3-fluoro-benzenesulfonyl chloride (2.64 ml, 20.0 mmol) was added to the reaction mixture, and stirred at room temperature for 1 hour. Water was added to the reaction mixture and extracted with ethyl acetate. The extract was dried over anhydrous magnesium sulfate, and then concentrated under reduced pressure. The resulting residue was purified by silica gel column chromatography (ethyl acetate:n-hexane=1:4 (v/v)) to give 4.4 g of the title compound. (Yield: 74.1%)

$^1$H-NMR (500 MHz, CDCl$_3$): 8.01 (s, 1H), 7.47-7.43 (m, 1H), 7.35-7.30 (m, 2H), 7.15 (d, 1H), 6.69 (t, 2H), 3.87 (s, 3H), 3.67 (s, 3H)

(Step 22-5) Preparation of 1-((3-fluorophenyl)sulfonyl)-4-methoxy-5-(2,4,6-trifluorophenyl)-1H-pyrrol-3-carbaldehyde Methyl 1-((3-fluorophenyl)sulfonyl)-4-methoxy-5-(2,4,6-trifluorophenyl)-1H-pyrrol-3-carboxylate (4.3 g, 9.7 mmol) prepared in Step 22-4 was dissolved in tetrahydrofuran (100.0 ml). Diisobutylaluminium hydride (1.0M tetrahydrofuran solution) (29.1 ml, 29.1 mmol) was added to the resulting solution at room temperature. The reaction mixture was stirred at room temperature for 1 hour, neutralized using 1N hydrochloric acid aqueous solution and then extracted with ethyl acetate. The extract was dried over anhydrous magnesium sulfate, and then concentrated under reduced pressure.

The resulting residue was dissolved in dichloromethane (100.0 ml) to which celite (4.3 g) and pyridinium chlorochromate (6.3 g, 29.1 mmol) were added. The reaction mixture was stirred at room temperature for 1 hour, and then filtered. The filtrate was concentrated under reduced pressure. The resulting residue was purified by silica gel column chromatography (ethyl acetate:n-hexane=1:2 (v/v)) to give 1.8 g of the title compound. (Yield: 44.9%)

$^1$H-NMR (500 MHz, CDCl$_3$): 9.89 (s, 1H), 8.01 (s, 1H), 7.49-7.45 (m, 1H), 7.37-7.31 (m, 2H), 7.15 (d, 1H), 6.70 (t, 2H), 3.68 (s, 3H)

(Step 22-6) Preparation of 1-(1-((3-fluorophenyl)sulfonyl)-4-methoxy-5-(2,4,6-trifluorophenyl)-1H-pyrrol-3-yl)-N-methylmethanamine 1-((3-fluorophenyl)sulfonyl)-4-methoxy-5-(2,4,6-trifluorophenyl)-1H-pyrrol-3-carbaldehyde (1.5 g, 3.6 mmol) prepared in Step 22-5 was dissolved in methanol (35.0 ml). Methylamine (9.8M methanol solution) (7.4 ml, 72.6 mmol) was added to the resulting solution and stirred at room temperature for 30 minutes. Sodium borohydride (1.4 g, 36.3 mmol) was added to the reaction mixture and stirred at room temperature for 30 minutes. Water was added to the reaction mixture, and extracted with ethyl acetate. The extract was dried over anhydrous magnesium sulfate, and then concentrated under reduced pressure. The resulting residue was purified by silica gel column chromatography (dichloromethane:methanol=10:1 (v/v)) to give 1.2 g of the title compound. (Yield: 84.9%)

$^1$H-NMR (500 MHz, MeOD): 7.51-7.52 (m, 1H), 7.47 (s, 1H), 7.43 (t, 1H), 7.36 (d, 1H), 7.23 (d, 1H), 6.91 (t, 2H), 3.59 (s, 2H), 3.50 (s, 3H), 2.39 (s, 3H)

(Step 22-7) Preparation of 1-(1-((3-fluorophenyl)sulfonyl)-4-methoxy-5-(2,4,6-trifluorophenyl)-1H-pyrrol-3-yl)-N-methylmethanamine hydrochloride 1-(1-((3-fluorophenyl)sulfonyl)-4-methoxy-5-(2,4,6-trifluorophenyl)-1H-pyrrol-3-yl)-N-methylmethanamine (1.2 g, 3.1 mmol) prepared in Step 22-6 was dissolved in ethylacetate (5.0 ml). Hydrochloric acid solution (2.0M diethyl ether solution) (3.1 ml, 6.1 mmol) was added to the resulting solution, stirred at room temperature for 1 hour and then filtered. The resulting solid was dried under reduced pressure to give 1.1 g of the title compound. (Yield: 77.6%)

Molecular weight: 464.86

$^1$H-NMR (500 MHz, MeOD): 7.64 (s, 1H), 7.60-7.56 (m, 1H), 7.49 (t, 1H), 7.37 (d, 1H), 7.26 (d, 1H), 6.95 (t, 2H), 4.08 (s, 2H), 3.52 (s, 3H), 2.70 (s, 3H)

The title compounds of the following additional examples were prepared in the preparation method similar to the method of Examples previously prepared, however, they were prepared by appropriately replacing the starting materials in compliance with the structure of the compounds to be produced with reference to the Reaction Schemes 1 to 3 in specification.

Example 1: Preparation of 1-(5-(2-fluorophenyl)-4-methoxy-1-((3-chlorophenyl)sulfonyl)-1H-pyrrol-3-yl)-N-methylmethanamine hydrochloride

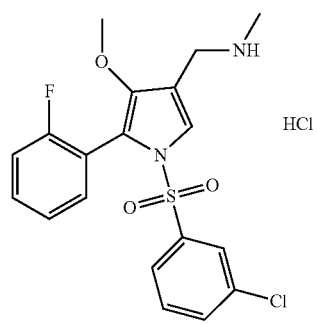 [SMILES: CNCc1cn(S(=O)(=O)c2cccc(Cl)c2)c(-c2ccccc2F)c1OC ; Cl]

Molecular weight: 445.33

$^1$H-NMR (500 MHz, CD$_3$OD): 7.69 (d, 1H), 7.66 (s, 1H), 7.54 (q, 1H), 7.49 (t, 1H), 7.40 (d, 1H), 7.28 (s, 1H), 7.21 (t, 1H), 7.15 (t, 1H), 7.08 (t, 1H), 4.05 (s, 2H), 3.44 (s, 3H), 2.70 (s, 3H)

Example 3: Preparation of 1-(5-(2-fluorophenyl)-4-methoxy-1-((3-methoxyphenyl)sulfonyl)-1H-pyrrol-3-yl)-N-methylmethanamine hydrochloride

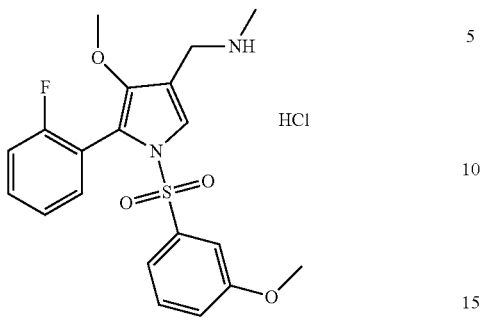

Molecular weight: 440.91
$^{1}$H-NMR (500 MHz, CD$_{3}$OD): 7.67 (s, 1H), 7.50 (q, 1H), 7.38 (t, 1H), 7.15-7.22 (m, 2H), 7.02-7.12 (m, 3H), 6.83 (s, 1H), 4.08 (s, 2H), 3.75 (s, 3H), 3.48 (s, 3H), 2.71 (s, 3H)

Example 4: Preparation of 1-(5-(2-fluorophenyl)-4-methoxy-1-((3-difluoromethoxyphenyl)sulfonyl)-1H-pyrrol-3-yl)-N-methylmethanamine hydrochloride

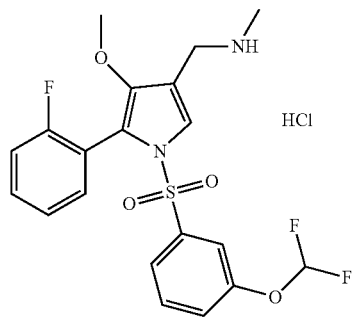 [SMILES: CNCc1cn(S(=O)(=O)c2cccc(OC(F)F)c2)c(-c2ccccc2F)c1OC ; Cl]

Molecular weight: 476.9
$^{1}$H-NMR (500 MHz, CD$_{3}$OD): 7.70 (s, 1H), 7.52-7.55 (m, 2H), 7.46 (d, 1H), 7.33 (d, 1H), 7.18 (t, 1H), 7.11-7.13 (m, 2H), 7.06 (t, 1H), 6.88 (t, 1H), 4.09 (s, 2H), 3.43 (s, 3H), 2.71 (s, 3H)

Example 5: Preparation of 1-(5-(2-chlorophenyl)-4-methoxy-1-((3-methoxyphenyl)sulfonyl)-1H-pyrrol-3-yl)-N-methylmethanamine hydrochloride

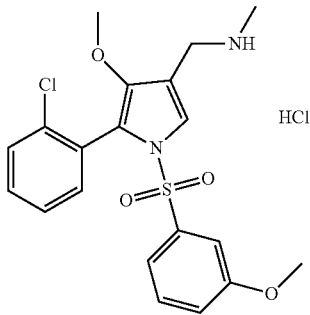 [SMILES: CNCc1cn(S(=O)(=O)c2cccc(OC)c2)c(-c2ccccc2Cl)c1OC ; Cl]

Molecular weight: 457.37
$^{1}$H-NMR (500 MHz, CD$_{3}$OD): 7.66 (s, 1H), 7.45 (t, 1H), 7.36-7.40 (m, 2H), 7.32 (t, 1H), 7.23 (d, 1H), 7.20 (dd, 1H), 7.04 (d, 1H), 6.82 (t, 1H), 4.08 (s, 2H), 3.76 (s, 3H), 3.41 (s, 3H), 2.71 (s, 3H)

Example 6: Preparation of 1-(5-(2-fluoro-4-chlorophenyl)-4-methoxy-1-((3-chlorophenyl)sulfonyl)-1H-pyrrol-3-yl)-N-methylmethanamine hydrochloride

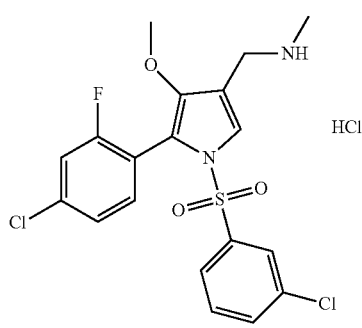 [SMILES: CNCc1cn(S(=O)(=O)c2cccc(Cl)c2)c(-c2ccc(Cl)cc2F)c1OC ; Cl]

Molecular weight: 479.77
$^{1}$H-NMR (500 MHz, CD$_{3}$OD): 7.70-7.72 (m, 2H), 7.52 (t, 1H), 7.44 (d, 1H), 7.31 (t, 1H), 7.27 (dd, 1H), 7.21 (dd, 1H), 7.15 (t, 1H), 4.08 (s, 2H), 3.46 (s, 3H), 2.71 (s, 3H)

Example 7: Preparation of 1-(5-(2-fluoro-4-chlorophenyl)-4-methoxy-1-((3-(trifluoromethyl)phenyl)sulfonyl)-1H-pyrrol-3-yl)-N-methylmethanamine hydrochloride

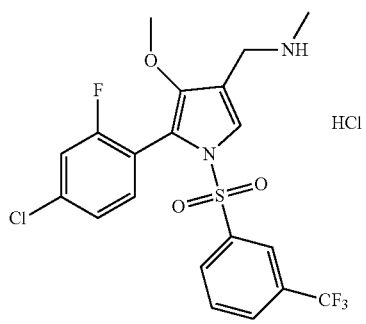 [SMILES: CNCc1cn(S(=O)(=O)c2cccc(C(F)(F)F)c2)c(-c2ccc(Cl)cc2F)c1OC ; Cl]

Molecular weight: 513.33
$^{1}$H-NMR (500 MHz, CDCl$_{3}$): 7.81 (d, 1H), 7.69 (d, 1H), 7.59-7.55 (m, 2H), 7.33 (s, 1H), 7.16-7.11 (m, 2H), 7.05 (d, 1H), 3.63 (s, 2H), 3.45 (s, 3H), 2.46 (s, 3H)

Example 9: Preparation of 1-(5-(2,4-difluorophenyl)-1-((3-(trifluoromethyl)phenyl)sulfonyl)-4-methoxy-1H-pyrrol-3-yl)-N-methylmethanamine hydrochloride

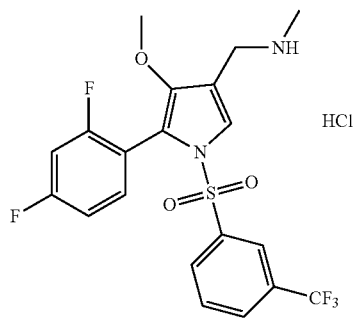 [SMILES: CNCc1cn(S(=O)(=O)c2cccc(C(F)(F)F)c2)c(-c2ccc(F)cc2F)c1OC ; Cl]

Molecular weight: 496.88
$^1$H-NMR (500 MHz, CDCl$_3$): 7.91 (d, 1H), 7.83 (d, 1H), 7.66 (t, H), 7.53 (s, 1H), 7.18-7.13 (q, 1H), 6.88 (t, 1H), 6.74 (t, 1H), 4.04 (s, 2H), 3.43 (s, 3H), 2.67 (s, 3H)

Example 10: Preparation of 1-(5-(2,4-difluorophenyl)-1-((3-methylphenyl)sulfonyl)-4-methoxy-1H-pyrrol-3-yl)-N-methylmethanamine hydrochloride

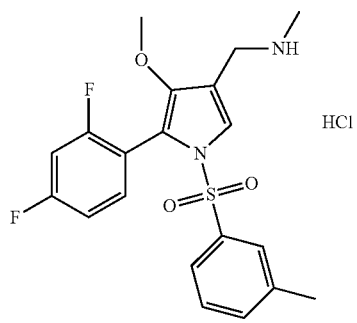 [SMILES: CNCc1cn(S(=O)(=O)c2cccc(C)c2)c(-c2ccc(F)cc2F)c1OC ; Cl]

Molecular weight: 442.91
$^1$H-NMR (500 MHz, CDCl$_3$): 7.78 (s, 1H), 7.46 (s, 1H), 7.36-7.20 (m, 3H), 7.15-7.10 (q, 1H), 6.86 (t, 1H), 6.74 (t, 1H), 4.03 (s, 2H), 3.47 (s, 3H), 2.65 (t, 3H), 2.33 (s, 3H)

Example 11: Preparation of 1-(5-(2,4-difluorophenyl)-1-((3-methoxyphenyl)sulfonyl)-4-methoxy-1H-pyrrol-3-yl)-N-methylmethanamine hydrochloride

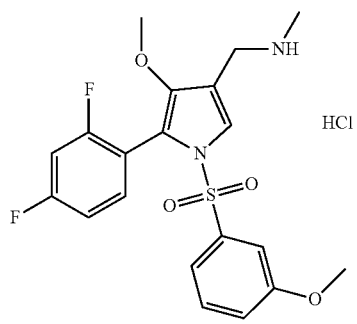 [SMILES: CNCc1cn(S(=O)(=O)c2cccc(OC)c2)c(-c2ccc(F)cc2F)c1OC ; Cl]

Molecular weight: 458.9
$^1$H-NMR (500 MHz, DMSO): 7.78 (d, 1H), 7.36 (m, 1H), 7.20-7.05 (m, 3H), 6.87 (m, 2H), 6.74 (t, 1H), 4.03 (d, 2H), 3.75 (d, 3H), 3.42 (d, 3H), 2.65 (s, 3H)

Example 12: Preparation of 1-(5-(2,4-difluorophenyl)-1-((3-difluoromethoxyphenyl)sulfonyl)-4-methoxy-1H-pyrrol-3-yl)-N-methylmethanamine hydrochloride

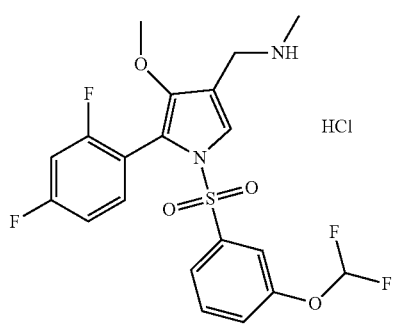 [SMILES: CNCc1cn(S(=O)(=O)c2cccc(OC(F)F)c2)c(-c2ccc(F)cc2F)c1OC ; Cl]

Molecular weight: 494.89
$^1$H-NMR (500 MHz, CDCl$_3$): 7.41 (m, 1H), 7.36 (s, 1H), 7.31 (d, 2H), 7.15-7.13 (m, 2H), 6.87 (t, 1H), 6.77 (t, 1H), 6.65-6.37 (t, 1H), 3.67 (s, 2H), 3.44 (s, 3H), 2.48 (s, 3H)

Example 13: Preparation of 1-(5-(2,6-difluorophenyl)-1-((3-fluorophenyl)sulfonyl)-4-methoxy-1H-pyrrol-3-yl)-N-methylmethanamine hydrochloride

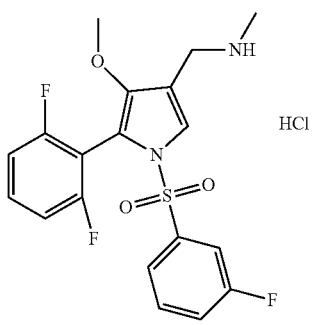 [SMILES: CNCc1cn(S(=O)(=O)c2cccc(F)c2)c(-c2c(F)cccc2F)c1OC ; Cl]

Molecular weight: 446.87
$^1$H-NMR (500 MHz, CD$_3$OD): 7.74 (s, 1H), 7.53-7.61 (m, 2H), 7.47 (t, 1H), 7.33 (d, 1H), 7.18 (d, 1H), 7.01 (t, 2H), 4.07 (s, 2H), 3.50 (s, 3H), 2.71 (s, 3H)

Example 14: Preparation of 1-(5-(2,6-difluorophenyl)-1-((3-chlorophenyl)sulfonyl)-4-methoxy-1H-pyrrol-3-yl)-N-methylmethanamine hydrochloride

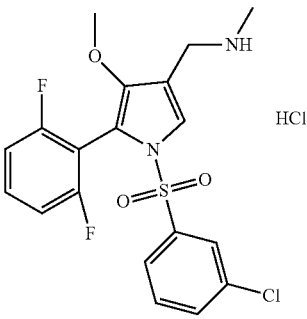 [SMILES: CNCc1cn(S(=O)(=O)c2cccc(Cl)c2)c(-c2c(F)cccc2F)c1OC ; Cl]

Molecular weight: 463.32
$^1$H-NMR (500 MHz, CD$_3$OD): 7.75 (s, 1H), 7.71 (d, 1H), 7.59-7.62 (m, 1H), 7.51 (t, 1H), 7.46 (d, 1H), 7.36 (s, 1H), 7.02 (t, 2H), 4.08 (s, 2H), 3.50 (s, 3H), 2.71 (s, 3H)

Example 15: Preparation of 1-(5-(2,6-difluorophenyl)-1-((3-(trifluoromethyl)phenyl)sulfonyl)-4-methoxy-1H-pyrrol-3-yl)-N-methylmethanamine hydrochloride

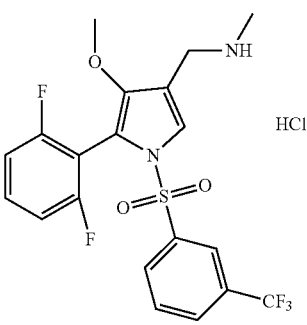 [SMILES: CNCc1cn(S(=O)(=O)c2cccc(C(F)(F)F)c2)c(-c2c(F)cccc2F)c1OC ; Cl]

Molecular weight: 466.85
$^1$H-NMR (500 MHz, CD$_3$OD): 8.03 (d, 1H), 7.83 (d, 1H), 7.76 (t, 1H), 7.64 (s, 1H), 7.59 (t, 1H), 6.99 (t, 1H), 4.05 (s, 2H), 3.49 (s, 3H), 2.69 (s, 3H)

Example 16: Preparation of 1-(5-(2,6-difluorophenyl)-1-((3-methylphenyl)sulfonyl)-4-methoxy-1H-pyrrol-3-yl)-N-methylmethanamine fumarate

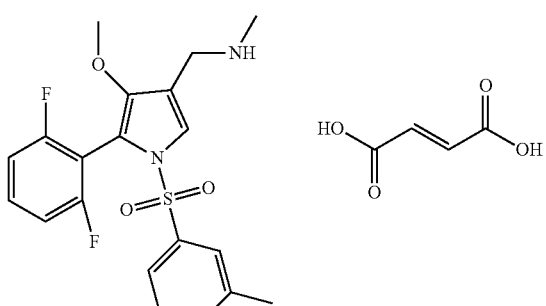

Molecular weight: 522.52
$^1$H-NMR (500 MHz, CD$_3$OD): 7.70 (d, 1H), 7.57 (t, 1H), 7.49 (d, 1H), 7.37 (t, 1H), 7.30 (d, 1H), 7.19 (s, 1H), 6.97 (t, 2H), 6.67 (s, 2H), 4.60 (s, 3H), 4.04 (d, 2H), 3.48 (s, 3H), 2.69 (t, 3H), 2.33 (s, 3H)

Example 17: Preparation of 1-(5-(2,6-difluorophenyl)-1-((3-methoxyphenyl)sulfonyl)-4-methoxy-1H-pyrrol-3-yl)-N-methylmethanamine hydrochloride

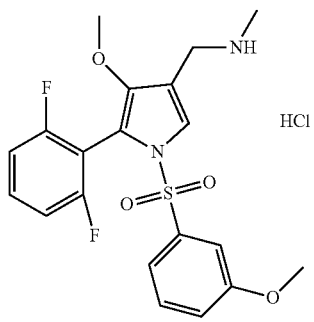 [SMILES: CNCc1cn(S(=O)(=O)c2cccc(OC)c2)c(-c2c(F)cccc2F)c1OC ; Cl]

Molecular weight: 458.9
$^1$H-NMR (500 MHz, CD$_3$OD): 7.71 (d, 1H), 7.57 (t, 1H), 7.39 (t, 1H), 7.22 (d, 1H), 7.08 (d, 1H), 6.99 (t, 1H), 6.90 (s, 1H), 4.03 (d, 2H), 3.77 (s, 3H), 3.49 (s, 3H), 2.68 (d, 3H)

Example 18: Preparation of 1-(5-(2,6-difluorophenyl)-1-((3-chloro-4-fluorophenyl)sulfonyl)-4-methoxy-1H-pyrrol-3-yl)-N-methylmethanamine hydrochloride

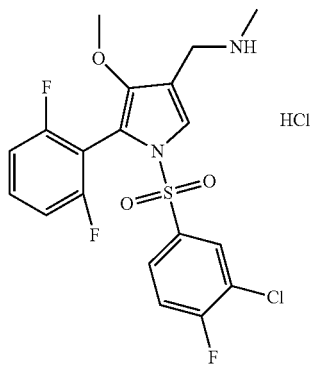 [SMILES: CNCc1cn(S(=O)(=O)c2ccc(F)c(Cl)c2)c(-c2c(F)cccc2F)c1OC ; Cl]

Molecular weight: 481.31
$^1$H-NMR (500 MHz, CD$_3$OD): 7.71 (s, 1H), 7.65-7.57 (m, 1H), 7.58-7.50 (m, 2H), 7.45 (t, 1H), 7.05 (t, 2H), 4.03 (s, 2H), 3.50 (s, 3H), 2.72 (s, 3H)

Example 19: Preparation of 1-(5-(2,6-difluorophenyl)-1-((3,4-difluorophenyl)sulfonyl)-4-methoxy-1H-pyrrol-3-yl)-N-methylmethanamine hydrochloride

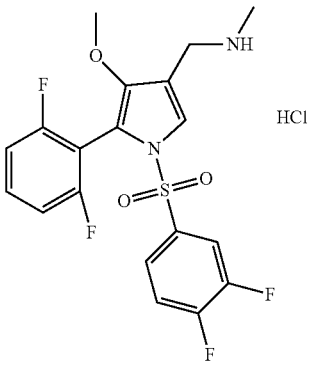 [SMILES: CNCc1cn(S(=O)(=O)c2ccc(F)c(F)c2)c(-c2c(F)cccc2F)c1OC ; Cl]

Molecular weight: 464.86
¹H-NMR (500 MHz, CD₃OD): 7.73 (s, 1H), 7.61 (t, 1H), 7.58-7.02 (m, 4H), 7.02 (t, 2H), 4.07 (s, 1H), 3.50 (s, 3H), 2.71 (s, 3H)

Example 20: Preparation of 1-(5-(2-fluoro-6-chlorophenyl)-1-((3-fluorophenyl)sulfonyl)-4-methoxy-1H-pyrrol-3-yl)-N-methylmethanamine hydrochloride

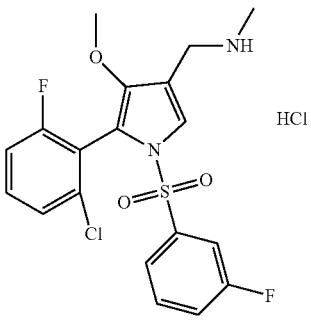 [SMILES: CNCc1cn(S(=O)(=O)c2cccc(F)c2)c(-c2c(F)cccc2Cl)c1OC ; Cl]

Molecular weight: 463.32
¹H-NMR (500 MHz, CD₃OD): 7.54-7.48 (m, 3H), 7.42 (t, 1H), 7.35 (d, 1H), 7.27 (d, 1H), 7.17 (d, 1H), 7.12 (t, 1H), 3.65 (s, 2H), 3.45 (s, 3H), 2.43 (s, 3H)

Example 21: Preparation of 1-(5-(2-fluoro-6-chlorophenyl)-1-((3-chlorophenyl)sulfonyl)-4-methoxy-1H-pyrrol-3-yl)-N-methylmethanamine hydrochloride

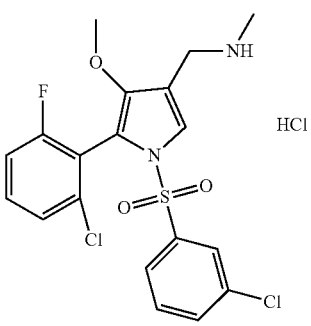 [SMILES: CNCc1cn(S(=O)(=O)c2cccc(Cl)c2)c(-c2c(F)cccc2Cl)c1OC ; Cl]

Molecular weight: 479.77
¹H-NMR (500 MHz, CD₃OD): 7.70 (s, 2H), 7.56-7.55 (m, 3H), 7.51-7.48 (m, 1H), 7.30 (d, 1H), 7.18-7.16 (m, 1H), 4.60 (s, 2H), 4.00 (s, 3H), 2.66 (s, 3H)

Example 23: Preparation of 1-(1-((3-chlorophenyl)sulfonyl)-4-methoxy-5-(2,4,6-trifluorophenyl)-1H-pyrrol-3-yl)-N-methylmethanamine hydrochloride

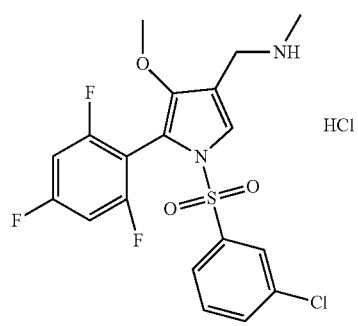 [SMILES: CNCc1cn(S(=O)(=O)c2cccc(Cl)c2)c(-c2c(F)cc(F)cc2F)c1OC ; Cl]

Molecular weight: 481.31
¹H-NMR (500 MHz, CD₃OD): 7.74-7.72 (m, 2H), 7.54 (t, 1H), 7.50 (d, 1H), 7.43 (t, 1H), 6.95 (t, 1H), 4.05 (s, 2H), 3.53 (s, 3H), 2.69 (s, 3H)

Example 24: Preparation of 1-(1-((3-trifluoromethylphenyl)sulfonyl)-4-methoxy-5-(2,4,6-trifluorophenyl)-1H-pyrrol-3-yl)-N-methylmethanamine hydrochloride

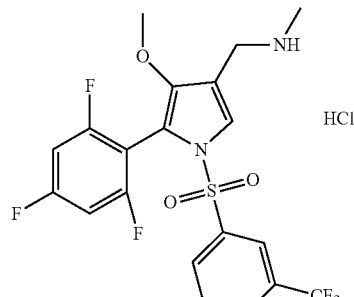

Molecular weight: 514.87
¹H-NMR (500 MHz, CD₃OD): 8.05 (d, 1H), 7.87 (d, 1H), 7.88-7.78 (m, 2H), 7.69 (s, 1H), 6.94-6.91 (m, 2H), 4.07 (s, 2H), 3.52 (s, 3H), 2.70 (s, 3H)

Example 25: Preparation of 1-(1-((3-methoxyphenyl)sulfonyl)-4-methoxy-5-(2,4,6-trifluorophenyl)-1H-pyrrol-3-yl)-N-methylmethanamine hydrochloride

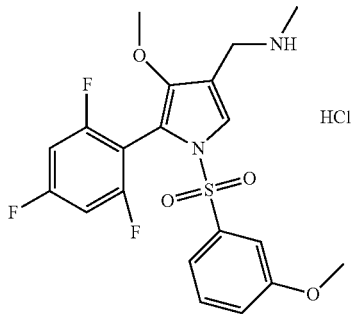 [SMILES: CNCc1cn(S(=O)(=O)c2cccc(OC)c2)c(-c2c(F)cc(F)cc2F)c1OC ; Cl]

Molecular weight: 476.90
¹H-NMR (500 MHz, CD₃OD): 7.74 (s, 1H), 7.44 (t, 1H), 7.25 (d, 1H), 7.12 (d, 1H), 6.95-6.91 (m, 3H), 4.07 (s, 2H), 3.80 (s, 3H), 3.52 (s, 3H), 2.71 (s, 3H)

Example 26: Preparation of 1-(1-((3,4-difluorophenyl)sulfonyl)-4-methoxy-5-(2,4,6-trifluorophenyl)-1H-pyrrol-3-yl)-N-methylmethanamine hydrochloride

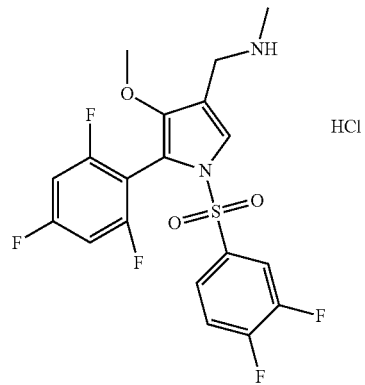 [SMILES: CNCc1cn(S(=O)(=O)c2ccc(F)c(F)c2)c(-c2c(F)cc(F)cc2F)c1OC ; Cl]

Molecular weight: 482.85
¹H-NMR (500 MHz, CD₃OD): 7.73 (s, 1H), 7.52-7.48 (m, 2H), 7.41-7.39 (m, 1H), 6.99-6.96 (m, 2H), 4.07 (s, 2H), 3.52 (s, 3H), 2.69 (s, 3H)

Example 27: Preparation of 1-(1-((3-fluorophenyl)sulfonyl)-4-methoxy-5-(2,3,6-trifluorophenyl)-1H-pyrrol-3-yl)-N-methylmethanamine hydrochloride

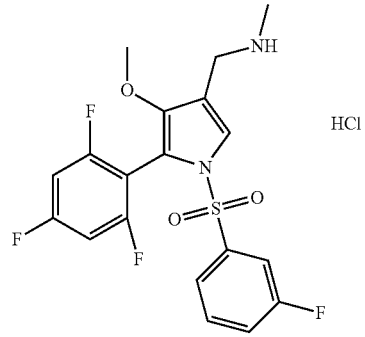 [SMILES: CNCc1cn(S(=O)(=O)c2cccc(F)c2)c(-c2c(F)cc(F)cc2F)c1OC ; Cl]

Molecular weight: 464.86
¹H-NMR (500 MHz, CD₃OD): 7.61 (s, 1H), 7.60~7.49 (m, 3H), 7.25 (d, 1H), 4.08 (s, 2H), 3.53 (s, 3H), 2.72 (s, 3H)

Example 28: Preparation of 1-(1-((3-chlorophenyl)sulfonyl)-4-methoxy-5-(2,3,6-trifluorophenyl)-1H-pyrrol-3-yl)-N-methylmethanamine hydrochloride

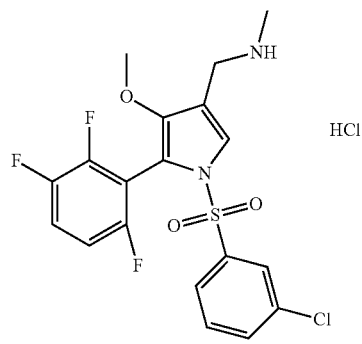

Molecular weight: 481.31
¹H-NMR (500 MHz, CD₃OD): 7.78 (s, 1H), 7.74 (d, 1H), 7.73~7.48 (m, 3H), 7.42 (d, 1H), 4.08 (s, 2H), 3.53 (s, 3H), 2.72 (s, 3H)

Example 29: Preparation of 1-(1-((3-trifluoromethylphenyl)sulfonyl)-4-methoxy-5-(2,3,6-trifluorophenyl)-1H-pyrrol-3-yl)-N-methylmethanamine hydrochloride

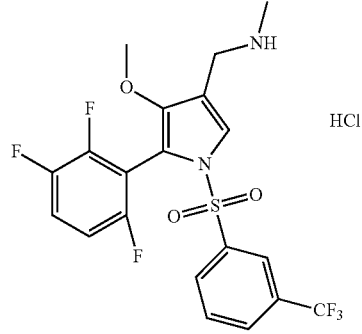 [SMILES: CNCc1cn(S(=O)(=O)c2cccc(Cl)c2)c(-c2c(F)ccc(F)c2F)c1OC ; Cl]

Molecular weight: 514.87
¹H-NMR (500 MHz, CD₃OD): 8.55 (d, 1H), 7.8~77.77 (m, 3H), 7.68 (s, 1H), 7.55~7.52 (m, 1H), 7.0-36.99 (m, 1H), 4.09 (s, 2H), 3.52 (s, 3H), 2.71 (s, 3H)

Example 30: Preparation of 1-(1-((3-methoxyphenyl)sulfonyl)-4-methoxy-5-(2,3,6-trifluorophenyl)-1H-pyrrol-3-yl)-N-methylmethanamine hydrochloride

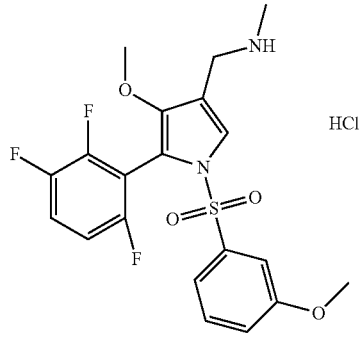 [SMILES: CNCc1cn(S(=O)(=O)c2cccc(OC)c2)c(-c2c(F)ccc(F)c2F)c1OC ; Cl]

Molecular weight: 476.9

$^1$H-NMR (500 MHz, CD$_3$OD): 7.77 (s, 1H), 7.54~7.48 (m, 1H), 7.43 (t, 1H), 7.26 (d, 1H), 7.11 (d, 1H), 7.04~6.99 (m, 1H), 6.93 (s, 1H), 4.89 (s, 2H), 3.79 (s, 3H), 3.52 (s, 3H), 2.71 (s, 3H)

Example 31: Preparation of 1-(5-(2,5-difluorophenyl)-1-((3-fluorophenyl)sulfonyl)-4-methoxy-1H-pyrrol-3-yl)-N-methylmethanamine hydrochloride

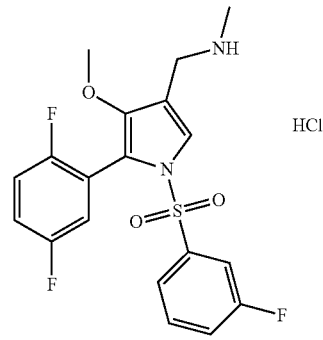 [SMILES: CNCc1cn(S(=O)(=O)c2cccc(F)c2)c(-c2cc(F)ccc2F)c1OC ; Cl]

Molecular weight: 446.87

$^1$H-NMR (500 MHz, CD$_3$OD): 7.71 (s, 1H), 7.54-7.58 (m, 1H), 7.47 (t, 1H), 7.32 (d, 1H), 7.27-7.30 (m, 1H), 7.18 (d, 1H), 7.08-7.12 (m, 1H), 6.90-6.93 (m, 1H), 4.08 (s, 2H), 3.49 (s, 3H), 2.72 (s, 3H)

Example 32: Preparation of 1-(5-(2,5-difluorophenyl)-1-((3-trifluoromethylphenyl)sulfonyl)-4-methoxy-1H-pyrrol-3-yl)-N-methylmethanamine hydrochloride

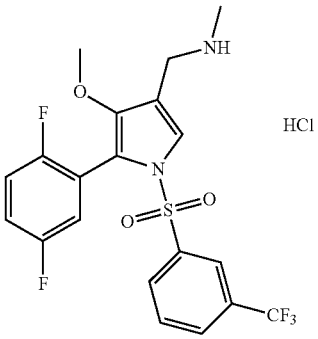 [SMILES: CNCc1cn(S(=O)(=O)c2cccc(C(F)(F)F)c2)c(-c2cc(F)ccc2F)c1OC ; Cl]

Molecular weight: 496.88

$^1$H-NMR (500 MHz, CD$_3$OD): 8.02 (d, 1H), 7.84 (d, 1H), 7.76-7.79 (m, 2H), 7.62 (s, 1H), 7.26-7.30 (m, 1H), 7.05-7.10 (m, 1H), 6.91-6.94 (m, 1H), 4.09 (s, 2H), 3.47 (s, 3H), 2.71 (s, 3H)

Example 33: Preparation of 1-(5-(2,5-difluorophenyl)-1-((3-methoxyphenyl)sulfonyl)-4-methoxy-1H-pyrrol-3-yl)-N-methylmethanamine hydrochloride

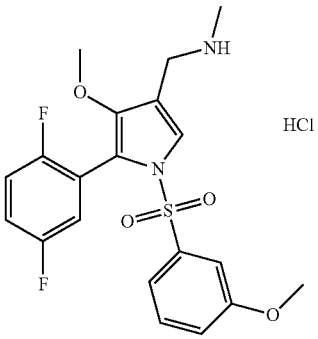 [SMILES: CNCc1cn(S(=O)(=O)c2cccc(OC)c2)c(-c2cc(F)ccc2F)c1OC ; Cl]

Molecular weight: 458.9

$^1$H-NMR (500 MHz, CD$_3$OD): 7.71 (s, 1H), 7.42 (t, 1H), 7.22-7.27 (m, 2H), 7.07-7.10 (m, 2H), 6.89 (t, 1H), 6.82-6.86 (m, 1H), 4.08 (s, 2H), 3.78 (s, 3H), 3.48 (s, 3H), 2.71 (s, 3H)

Test Example 1: Inhibitory Effects on Proton Pump (H$^+$/K$^+$-ATPase) Activity The inhibitory effects on proton pump (H$^+$/K$^+$-ATPase) activity of the compounds prepared in Examples 2, 8 and 22 were measured as follows.

Gastric vesicles were prepared from a hog stomach in accordance with the known method (Edd C. Rabon et al., Preparation of Gastric H$^+$, K$^+$-ATPase., Methods in enzymology, vol. 157 Academic Press Inc., (1988), pp. 649-654). The protein contents of gastric vesicles thus prepared were quantitatively measured with Bicinchoninic Acid (BCA) kit (Thermo Co.).

80 ul of (a predetermined concentration of a test compound, 0.5% DMSO, 2.5 mM $MgCl_2$, 12.5 mM KCl, 1.25 mM EDTA, 60 mM Tris-HCl, pH7.4) was added to each well of 96-well plate. 10 ul of the reaction solution containing gastric vesicles (60 mmol/l, Tris-HCl buffer solution, pH 7.4), and 10 ul of Tris buffer solution containing adenosine triphosphate (10 mM ATP, Tris-HCl buffer solution, pH 7.4) were added to each well and subjected to enzymatic reaction at 37° C. for 40 minutes. 50 ul of malachite green solution (0.12% malachite green solution in 6.2N sulfuric acid, 5.8% ammonium molybdenum and 11% Tween 20 were mixed at a ratio of 100:67:2) was added thereto to stop the enzyme reaction, and 50 ul of 15.1% sodium citrate was added thereto. The amount of monophosphate (Pi) in the reaction solution was measured at 570 nm by using a microplate reader (FLUOstar Omega, BMG Co.). The inhibition rate (%) was measured from the activity value of the control group and the activity value of the test compound at various concentrations, and the concentration ($IC_{50}$) that inhibits $H^+/K^+$-ATPase activity by 50% was calculated from each % inhibition value of the compounds using Logistic 4-parameter function of Sigmaplot8.0 program. The results are shown in Table 1 below.

TABLE 1

|  | $IC_{50}$ |
| --- | --- |
| Example 2 | 0.015 uM |
| Example 8 | 0.024 uM |
| Example 22 | 0.014 uM |

Test Example 2. Inhibitory Effects on Basal Gastric Acid Secretion in Pylorus-Ligated Rats Inhibitory effects of the compounds prepared in Examples 2, 8 and 22 on basal gastric acid secretion were measured according to Shay's rat model (Shay, H., et al., 1945, gastroenterology, 5, p 43-61). Male Sprague Dawley (SD) rats (body weight 180-220 g) were divided into 4 groups (n=6-7) and fasted for 18 hours with free access to water. Under isoflurane anesthesia, the abdomens of the rats were incised and then the pylorus was ligated. Immediately after ligation, control group was administered with 2 mL/kg of 0.5% methyl cellulose (MC) aqueous solution into the duodenum, and the other groups were administered with test compounds suspended in 0.5% methyl cellulose (MC) aqueous solution at a dose of 2.0 mg/kg/2 ml. 5 hours after ligation, the test animals were sacrificed, and gastric contents were removed. The removed contents were centrifuged at 4,000×g for 10 minutes and the supernatant was separated to obtain the gastric juice. The amount and pH of the gastric juice were measured and the acidity in the gastric juice was measured by 0.1N NaOH volume (ueq/mL) required for the titration of gastric acid to pH 7.0. Total acid output was measured by multiplying the acidity of the gastric juice by the amount of the gastric juice. % inhibitory activity of test compounds were calculated according to the following equation, and the results are shown in Table 2.

% inhibitory activity of test compound=[(total acid output of control group-total acid output of the group treated with test compounds)/total acid output of control group]×100    [Equation 1]

TABLE 2

|  | % inhibitory activity |
| --- | --- |
| Example 2 | 93.5% |
| Example 8 | 90.5% |
| Example 22 | 88.1% |

Test Example 3: Gastric Damage Inhibitory Activity Against Indomethacin-Induced Gastric Damage in Rats The inhibitory activity against the gastric damage of the compounds prepared in Examples 2 and 8 was measured using indomethacin model (Chiou., Et al., 2005, gastroenterology, 128, p 63-73). Male Sprague Dawley (SD) rats (body weight 180-220 g) was divided into 5 groups (n=10) and fasted for 24 hours with free access to water. Control group was orally administered with 5 mL/kg of 0.5% methyl cellulose (MC) aqueous solution, and the other groups were orally administered with test compounds suspended in 0.5% methyl cellulose (MC) aqueous solution at a dose of 2.0 mg/kg/5 ml. For comparison, the compound of Example 134 (Comparative Example 1) and the compound of Example 165 (Comparative Example 2) in International Patent Publication No. WO 2006/036024 were orally administered at a dose of 2.0 mg/kg/5 ml by suspending 0.5% methylcellulose (MC) aqueous solution, respectively. 1 hour after oral administration, indomethacin was orally administered at a dose of 80 mg/kg/10 ml. After 4 hours and 30 minutes, the test animals were sacrificed to remove the stomach. The surface of the removed stomach was washed with saline solution and then half thereof was incised along a greater curvature of stomach. The incised stomach was placed on a fixture, fixed by a fixing pin while spreading out using a forcep and then the gastric damage area was measured. % Inhibitory activity of test compounds was calculated according to the following Equation 2, and the results are shown in Table 3.

% Inhibitory activity of test compound=[1−(gastric damage area % of the group treated with test compounds)/(gastric damage area % of control group)]×100    [Equation 2]

TABLE 3

|  | % inhibitory activity |
| --- | --- |
| Example 2 | 91.8% |
| Example 8 | 92.2% |
| Comparative Example 1 | 66.8% |
| Comparative Example 2 | 44.4% |

Test Example 4: Antimicrobial Activity Against *H. pylori*

The antimicrobial activity against *H. pylori* of the compounds prepared in the Examples 8 and 22 was evaluated by measuring the minimum inhibitory concentration (MIC) values through the susceptibility testing by the agar dilution method. *H. pylori* strains were furnished from *Helicobacter* isolated strain Bank (HpKTCC, KNMRRC) in the Microbiology Classroom of the Professional Graduate School of Medicine in Gyeongsang National University, South Korea. The test material dissolved in DMSO was subjected to two fold serial dilution with a sterile buffer to prepare a sample solution. At this time, each concentration of the serially diluted solution was adjusted to become 10 times the concentration used for the susceptibility testing. Thus, the concentration was adjusted so as to be added at a volume of 1/10 during preparation of the medium. While warming a water tank to 55 to 60° C., 5 ml of the sample solution with each concentration of the serially diluted solution warmed at the same temperature was added to Brucella agar medium (each 45 ml aliquot) containing 10% bovine serum, and prepared to have a final test concentration (test concentration: 5000 ug/ml, 2500 ug/ml, 1250 ug/ml, 625 ug/ml, 312.5 ug/ml, 150 ug/ml, 75 ug/ml, 37.5 ug/ml, 18.75 ug/ml, 9 ug/ml, 4.5 ug/ml, 2.25 ug/ml). Before the medium was hardened, it was divided and dispensed into two petri dishes to prepare an agar plate medium. *H. pylori* cultured in Brucella agar medium was prepared into each bacterial suspension with PBS ($5.0 \times 10^8$ CFU/mL), and dispensed in Steers multiple inoculator well. Bacterium were inoculated on the surface of the plate medium toward a high concentration side of substance from a low concentration side of substance using steers multiple inoculator. After culturing in 10% $CO_2$ incubator at 37° C. for 5 days, the presence or absence of growth of each bacteria was visually identified to determine the minimum inhibitory concentration (MIC, the lowest concentration where bacterium have not been observed). The results are shown in Tables 4 and 5 below.

TABLE 4

| No. | Bank accession number | General name (Strain) | MIC (ug/ml) Example 8 | MIC (ug/ml) Example 22 |
|---|---|---|---|---|
| 1 | HPKTCC B0508 | CH24 | 75 | 75 |
| 2 | HPKTCC B0582 | CH94 | 37.5 | 75 |
| 3 | HPKTCC B0494 | CH173 | 75 | 75 |
| 4 | HPKTCC B0498 | CH189 | 75 | 75 |
| 5 | HPKTCC B0500 | CH192 | 75 | 75 |
| 6 | HPKTCC B0516 | CH272 | 75 | 75 |
| 7 | HPKTCC B0524 | CH381 | 75 | 75 |
| 8 | HPKTCC B0536 | CH498 | 75 | 75 |
| 9 | HPKTCC B0537 | CH502 | 75 | 75 |
| 10 | HPKTCC B0548 | CH541 | 75 | 75 |
| 11 | HPKTCC B0558 | CH609 | 75 | 75 |
| 12 | HPKTCC B0560 | CH631 | 75 | 75 |
| 13 | HPKTCC B0564 | CH674 | 75 | 75 |
| 14 | HPKTCC B0556 | CH588 | 75 | 75 |
| 15 | HPKTCC B0562 | CH635 | 75 | 75 |
| 16 | HPKTCC B0541 | CH523 | 75 | 75 |
| 17 | HPKTCC B0522 | CH369 | 75 | 75 |
| 18 | HPKTCC B0559 | CH612 | 75 | 75 |
| 19 | HPKTCC B0487 | CH1056 | 75 | 75 |
| 20 | HPKTCC B0007 | 52 | 75 | 75 |
| 21 | HPKTCC B0004 | 45 | 75 | 75 |
| 22 | HPKTCC B0017 | 118 | 150 | 75 |
| 23 | HPKTCC B0021 | 127 | 75 | 75 |
| 24 | HPKTCC B0024 | 134 | 75 | 75 |
| 25 | HPKTCC B0040 | 164 | 75 | 75 |
| 26 | HPKTCC B0051 | 193 | 75 | 75 |
| 27 | HPKTCC B0606 | CJH7 | 75 | 75 |
| 28 | HPKTCC B0610 | CJH9 | 75 | 75 |
| 29 | HPKTCC B0594 | CJH31 | 75 | 75 |
| 30 | HPKTCC B0595 | CJH33 | 75 | 75 |

TABLE 5

| No. | Bank accession number | General name (Strain) | MIC (ug/ml) Example 8 | MIC (ug/ml) Example 22 |
|---|---|---|---|---|
| 31 | HPKTCC B0599 | CJH50 | 75 | 75 |
| 32 | HPKTCC B0596 | CJH43 | 75 | 75 |
| 33 | HPKTCC B0589 | CJH13 | 75 | 75 |
| 34 | HPKTCC B0587 | CJH10 | 75 | 75 |
| 35 | HPKTCC B0608 | CJH8 | 37.5 | 75 |
| 36 | HPKTCC B0100 | 26695 | 75 | 75 |
| 37 | HPKTCC B3412 | 26695 CHGKG | 150 | 150 |
| 38 | HPKTCC B0006 | 51 | 75 | 75 |
| 39 | HPKTCC B0748 | J99 | 75 | 75 |
| 40 | HPKTCC B0047 | 183 | 150 | 75 |
| 41 | HPKTCC B0055 | 198 | 75 | 75 |
| 42 | HPKTCC B0058 | 205 | 75 | 75 |
| 43 | HPKTCC B0061 | 210 | 75 | 75 |
| 44 | HPKTCC B0068 | 221 | 75 | 75 |
| 45 | HPKTCC B0071 | 228 | 75 | 75 |
| 46 | HPKTCC B0088 | 302 | 75 | 75 |
| 47 | HPKTCC B0075 | 236 | 75 | 75 |
| 48 | HPKTCC B0496 | CH175 | 75 | 75 |
| 49 | HPKTCC B0074 | 235 | 75 | 75 |
| 50 | HPKTCC B0722 | G88001 | 75 | 75 |
| 51 | HPKTCC B0725 | G88007 | 75 | 75 |
| 52 | HPKTCC B0020 | 126 | 150 | 75 |
| 53 | HPKTCC B0026 | 138 | 75 | 75 |
| 54 | HPKTCC B0023 | 133 | 37.5 | 75 |
| 55 | HPKTCC B0035 | 156 | 150 | 75 |
| 56 | HPKTCC B0037 | 159 | 150 | 75 |
| 57 | HPKTCC B0233 | 92-82-1 | 75 | 75 |
| 58 | HPKTCC B0152 | 92-157 | 75 | 75 |
| 59 | HPKTCC B0182 | 92-33-1 | 75 | 75 |
| 60 | HPKTCC B3392 | SS1-P-4' | 37.5 | 75 |

Test Example 5: Gastric Damage Inhibitory Activity Against 100% Ethanol (EtOH)-Induced Gastric Damage in Rats, and Effect of Enhancing Defensive Factors (Mucus)

The inhibitory activity and defensive factor-enhancing effects of the compound prepared in Example 8 were measured using 100% ethanol (EtOH)-induced gastric damage model (Paul V. Tan et al., 2002, Journal of Ethnopharmacology, 82, p 69-74). Male Sprague Dawley (SD) rats (body weight 180-200 g) was fasted for 24 hours with free access to water. Control group was orally administered with 5 mL/kg of 0.5% methyl cellulose (MC) aqueous solution, and the other groups were orally administered with test compounds suspended in 0.5% MC aqueous solution at a dose of 3.0, 10.0 and 30.0 mg/kg/5 mL. For comparison, the compound of Example 134 (Comparative Example 1), the compound of Example 165 (Comparative Example 2) and the compound of Example 166 (Comparative Example 3) in International Patent Publication No. WO2006/036024 were orally administered at the same dose by suspending 0.5% MC aqueous solution, respectively. 1 hour after oral administration, 1 mL of 100% EtOH was orally administered. 1 hour after EtOH administration, the test animals were sacrificed to remove the stomach. Ten in the total 20 animals scraped the mucus of stomach with a slide glass and the mucus contents were analyzed to calculate $ED_{50}$. The results were shown in Table 6. For the remaining 10 animals, the surface of the removed stomach was washed with a saline solution and then half thereof was incised along a greater curvature of stomach. The incised stomach was placed on a fixture, fixed by a fixing pin while spreading out using a forcep and then the gastric damage area was measured to calculate $ED_{50}$. The results are shown in Table 7.

TABLE 6

| | Mucus secretion $ED_{50}$ (mg/kg) |
|---|---|
| Example 8 | 12.2 |
| Comparative Example 1 | 26.9 |
| Comparative Example 2 | 21.6 |
| Comparative Example 3 | 22.1 |

TABLE 7

| | Gastric index $ED_{50}$ (mg/kg) |
|---|---|
| Example 8 | 13.4 |
| Comparative Example 1 | 29.5 |
| Comparative Example 2 | 30.9 |
| Comparative Example 3 | 19.2 |

From the results of Test Examples 1 to 5, it could be seen that the compounds according to the present invention had not only excellent proton pump inhibitory activity, gastric damage-inhibiting activity and defensive factor-enhancing effects, but also excellent eradication activity against *H. pylori*. In particular, the compound according to the present invention had not only excellent proton pump inhibitory activity, gastric damage-inhibiting activity and defensive factor-enhancing effects, but also excellent eradication activity against *H. pylori*, as compared with a structurally similar compound, for example, a compound either having no substituent or substituted with methyl at position 4 of pyrrole.

Test Example 6. Inhibitory Effects on GPCR

In order to confirm whether the compounds prepared in the above Examples act as an agonist or antagonist against GPCR Target, Calcium Flux assay was performed in an assay plate in which the compounds prepared in the Examples, vehicle controls, and reference compounds were added, using a Fluorometric imaging plate reader (FLIPR tetra) equipment.

Calcium Flux assay was evaluated by entrusting the GPCR profiler assay in Safety panel assays with Eurofins. By using the Fluo-8AM calcium dye, excitation was measured at a wavelength in the range of 470 to 495 nm and Emission was measured at a wavelength in the range of 515-575 nm. GPCR Assay Buffer for Calcium Flux assay was prepared by adding 20 mM of HEPES and 2.5 mM of Probenecid to Hanks Balanced Salt Solution (HBSS) to have pH 7.4. The Compounds of Examples for evaluation of the GPCR were diluted with DMSO at a concentration of 10 mM to make a stock and then prepared by diluting in the GPCR Assay Buffer at the concentration equivalent to three times the final concentration. First, for the evaluation of GPCRs, the inhibitory activity of the compounds of the Examples was evaluated at a single concentration of 10 uM, and then the respective selected targets were four fold-diluted from 10 uM to the low side to calculate 50% inhibitory concentration ($IC_{50}$), prepared at the total 8 concentrations of 10, 2.5, 0.62, 0.15, 0.04, 0.01, 0.0024, 0.0006 uM, and Calcium Flux assay for GPCR was conducted. In order to evaluate the agonist and antagonist, % inhibition rate against GPCR activity before and after treatment of the compounds and the inhibitory activity of the compounds of the Examples were determined.

As a result, when the efficacy of alpha-heth-5-HT and acetylcholine of the compounds prepared in the Examples was 100%, the inhibition rate (%) at a single concentration of 10 uM was evaluated and shown in Table 8. 50% inhibitory concentrations ($IC_{50}$, uM) for some compounds prepared in the Examples having excellent inhibitory rate was calculated and shown in Table 9 below.

TABLE 8

| Example | 5-HT2A | M1 | M2 |
|---|---|---|---|
| 1 | 96.4 | 99.6 | 66.5 |
| 2 | 39.5 | 92.7 | -4.7 |
| 3 | 94.0 | 87.0 | 76.9 |
| 4 | 96.0 | 55.8 | 22.0 |
| 5 | 69.1 | 93.7 | 75.1 |
| 6 | 101.9 | 93.1 | 15.1 |
| 7 | 42.3 | 65.6 | 0.8 |
| 8 | 101.7 | 101.3 | 100.7 |
| 9 | 61.1 | 74.7 | 18.3 |
| 10 | 100.9 | 96.2 | 77.6 |
| 11 | 101.7 | 97.2 | 79.4 |
| 12 | 101.4 | 93.1 | 28.7 |
| 13 | 101.8 | 100.2 | 99.4 |
| 14 | 99.9 | 94.9 | 48.1 |
| 15 | 30.1 | 87.1 | 62.1 |
| 16 | 101.9 | 95.4 | 69.7 |
| 17 | 101.9 | 85.2 | 60.1 |
| 18 | 98.1 | 91.2 | 42.1 |
| 19 | 101.8 | 100.8 | 101.8 |
| 20 | 99.2 | 102.7 | 90.5 |
| 22 | 102.1 | 98.0 | 100.3 |
| 24 | 62.2 | 93.4 | 22.0 |
| 26 | 99.0 | 101.2 | 89.2 |
| 27 | 99.1 | 101.1 | 100.3 |
| 28 | 97.6 | 99.4 | 61.9 |
| 29 | 35.7 | 68.4 | 19.4 |
| 30 | 100.4 | 94.3 | 43.0 |
| 31 | 101.3 | 100.0 | 98.6 |
| 32 | 10.6 | 52.6 | 10.8 |
| 33 | 96.7 | 81.5 | 29.0 |

TABLE 9

| Example | 5-HT2A | M1 | M2 |
|---|---|---|---|
| 1 | 0.25 | 1.7 | — |
| 3 | 0.18 | — | — |
| 4 | 0.85 | — | — |
| 6 | 0.16 | ~3.0 | — |
| 8 | 0.11 | 0.14 | 0.65 |
| 10 | 0.36 | 1.3 | — |
| 11 | 0.2 | 1.8 | — |
| 13 | 0.076 | 0.11 | 0.51 |
| 14 | 0.21 | -2.2 | — |
| 16 | 0.058 | 1.9 | — |
| 17 | 2.2 | — | — |
| 18 | 0.21 | ~2.1 | — |
| 19 | 0.12 | 0.43 | 0.82 |
| 22 | 0.033 | 0.37 | 1.0 |
| 24 | 0.062 | >1.0 | >10.0 |
| 27 | 0.057 | 0.051 | 0.18 |
| 28 | 0.067 | 0.55 | — |
| 30 | — | 1.4 | — |
| 31 | 0.042 | 0.073 | — |
| 33 | 1.7 | — | — |

As shown in Table 8, it could be seen that the compounds prepared in the Examples had high inhibition rate against 5-HT2A, M1 and M2 receptors and thus could be used as antagonist of these receptors. Further, as shown in Table 9, the compounds having high inhibition rate against 5-HT2A, M1 and M2 receptors exhibited excellent inhibitory effects on the receptors even at a small amount of 3 uM or less.

What is claimed is:
1. A compound represented by the following Chemical Formula 1 or a pharmaceutically acceptable salt thereof:

[Chemical Formula 1]

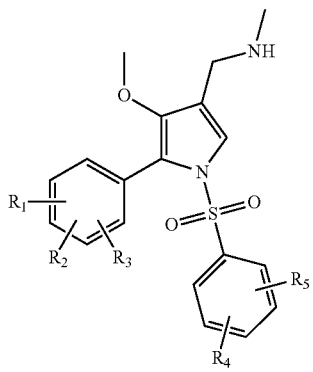

in Chemical Formula 1, $R_1$, $R_2$ and $R_3$ are each independently hydrogen or halogen, with the proviso that $R_1$, $R_2$ and $R_3$ cannot be hydrogen simultaneously, and $R_4$ and $R_5$ are each independently hydrogen, halogen, $C_{1-4}$ alkyl, $C_{1-4}$ alkoxy, $C_{1-4}$ haloalkyl, or $C_{1-4}$ haloalkoxy, with the proviso that $R_4$ and $R_5$ cannot be hydrogen simultaneously.

2. The compound or a pharmaceutically acceptable salt thereof according to claim 1, wherein $R_1$, $R_2$ and $R_3$ are each independently hydrogen, fluoro, or chloro, with the proviso that $R_1$, $R_2$ and $R_3$ cannot be hydrogen simultaneously.

3. The compound or a pharmaceutically acceptable salt thereof according to claim 1, wherein $R_4$ and $R_5$ are each independently hydrogen, chloro, fluoro, methyl, trifluoromethyl, methoxy, or difluoromethoxy, with the proviso that $R_4$ and $R_5$ cannot be hydrogen simultaneously.

4. The compound or a pharmaceutically acceptable salt thereof according to claim 1, wherein the compound is represented by the following Chemical Formula 1-1:

[Chemical Formula 1-1]

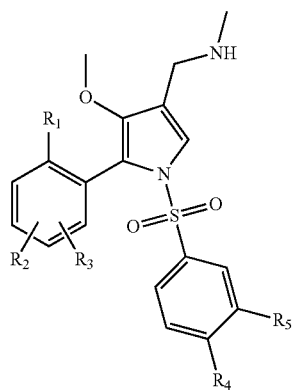

in Chemical Formula 1-1, $R_1$ to $R_5$ are as defined in claim 1.

5. The compound or a pharmaceutically acceptable salt thereof according to claim 4, wherein $R_1$, $R_2$ and $R_3$ are each independently hydrogen, fluoro, or chloro, with the proviso that $R_1$, $R_2$ and $R_3$ cannot be hydrogen simultaneously.

6. The compound or a pharmaceutically acceptable salt thereof according to claim 4, wherein $R_1$ is halogen, and $R_2$ and $R_3$ are each independently hydrogen, or halogen.

7. The compound or a pharmaceutically acceptable salt thereof according to claim 4, wherein $R_1$ is fluoro, and $R_2$ and $R_3$ are each independently hydrogen, fluoro, or chloro, or $R_1$ is chloro, and $R_2$ and $R_3$ are hydrogen.

8. The compound or a pharmaceutically acceptable salt thereof according to claim 4, wherein $R_4$ and $R_5$ are each independently hydrogen, chloro, fluoro, methyl, trifluoromethyl, methoxy, or difluoromethoxy, with the proviso that $R_4$ and $R_5$ cannot be hydrogen simultaneously.

9. The compound or a pharmaceutically acceptable salt thereof according to claim 4, wherein $R_4$ is halogen, and $R_5$ is chloro, fluoro, methyl, trifluoromethyl, methoxy, or difluoromethoxy, or $R_4$ and $R_5$ are each independently chloro, or fluoro.

10. The compound or a pharmaceutically acceptable salt thereof according to claim 4, wherein $R_1$ is fluoro, and $R_2$ and $R_3$ are each independently hydrogen, or fluoro, $R_4$ is hydrogen, and $R_5$ is chloro, or trifluoromethyl.

11. The compound or a pharmaceutically acceptable salt thereof according to claim 1, wherein the compound is selected from the group represented by the following Chemical Formulae 1-2 to 1-4:

[Chemical Formula 1-2]

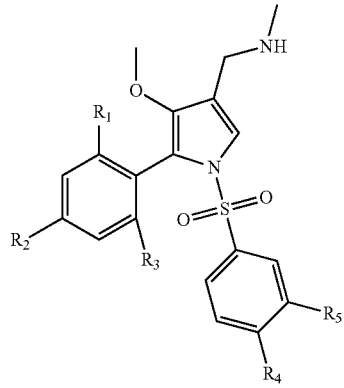

[Chemical Formula 1-3]

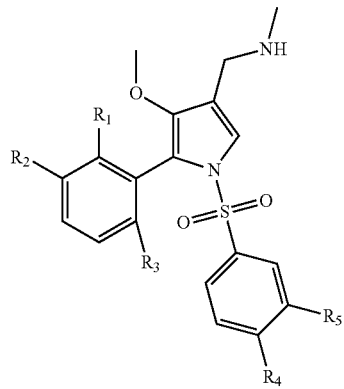

[Chemical Formula 1-4]

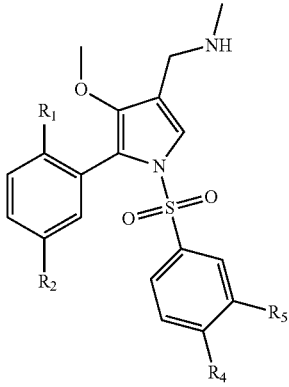

in Chemical Formulae 1-2 to 1-4,
$R_1$ to $R_5$ are as defined in claim 1.

12. The compound or a pharmaceutically acceptable salt thereof according to claim 1, wherein the compound is selected from the group consisting of the following compounds:
1) 1-(5-(2-fluorophenyl)-4-methoxy-1-((3-chlorophenyl)sulfonyl)-1H-pyrrol-3-yl)-N-methylmethanamine;
2) 1-(5-(2-fluorophenyl)-4-methoxy-1-((3-(trifluoromethyl)phenyl)sulfonyl)-1H-pyrrol-3-yl)-N-methylmethanamine;
3) 1-(5-(2-fluorophenyl)-4-methoxy-1-((3-methoxyphenyl)sulfonyl)-1H-pyrrol-3-yl)-N-methylmethanamine;
4) 1-(5-(2-fluorophenyl)-4-methoxy-1-((3-difluoromethoxyphenyl)sulfonyl)-1H-pyrrol-3-yl)-N-methylmethanamine;
5) 1-(5-(2-chlorophenyl)-4-methoxy-1-((3-methoxyphenyl)sulfonyl)-1H-pyrrol-3-yl)-N-methylmethanamine;
6) 1-(5-(2-fluoro-4-chlorophenyl)-4-methoxy-1-((3-chlorophenyl)sulfonyl)-1H-pyrrol-3-yl)-N-methylmethanamine;
7) 1-(5-(2-fluoro-4-chlorophenyl)-4-methoxy-1-((3-(trifluoromethyl)phenyl)sulfonyl)-1H-pyrrol-3-yl)-N-methylmethanamine;
8) 1-(5-(2,4-difluorophenyl)-1-((3-fluorophenyl)sulfonyl)-4-methyoxy-1H-pyrrol-3-yl)-N-methylmethanamine;
9) 1-(5-(2,4-difluorophenyl)-1-((3-(trifluoromethyl)phenyl)sulfonyl)-4-methoxy-1H-pyrrol-3-yl)-N-methylmethanamine;
10) 1-(5-(2,4-difluorophenyl)-1-((3-methylphenyl)sulfonyl)-4-methoxy-1H-pyrrol-3-yl)-N-methylmethanamine;
11) 1-(5-(2,4-difluorophenyl)-1-((3-methoxyphenyl)sulfonyl)-4-methoxy-1H-pyrrol-3-yl)-N-methylmethanamine;
12) 1-(5-(2,4-difluorophenyl)-1-((3-difluoromethoxyphenyl)sulfonyl)-4-methoxy-1H-pyrrol-3-yl)-N-methylmethanamine;
13) 1-(5-(2,6-difluorophenyl)-1-((3-fluorophenyl)sulfonyl)-4-methoxy-1H-pyrrol-3-yl)-N-methylmethanamine;
14) 1-(5-(2,6-difluorophenyl)-1-((3-chlorophenyl)sulfonyl)-4-methoxy-1H-pyrrol-3-yl)-N-methylmethanamine;
15) 1-(5-(2,6-difluorophenyl)-1-((3-(trifluoromethyl)phenyl)sulfonyl)-4-methoxy-1H-pyrrol-3-yl)-N-methylmethanamine;
16) 1-(5-(2,6-difluorophenyl)-1-((3-methylphenyl)sulfonyl)-4-methoxy-1H-pyrrol-3-yl)-N-methylmethanamine;
17) 1-(5-(2,6-difluorophenyl)-1-((3-methoxyphenyl)sulfonyl)-4-methoxy-1H-pyrrol-3-yl)-N-methylmethanamine;
18) 1-(5-(2,6-difluorophenyl)-1-((3-chloro-4-fluorophenyl)sulfonyl)-4-methoxy-1H-pyrrol-3-yl)-N-methylmethanamine;
19) 1-(5-(2,6-difluorophenyl)-1-((3,4-difluorophenyl)sulfonyl)-4-methoxy-1H-pyrrol-3-yl)-N-methylmethanamine;
20) 1-(5-(2-fluoro-6-chlorophenyl)-1-((3-fluorophenyl)sulfonyl)-4-methoxy-1H-pyrrol-3-yl)-N-methylmethanamine;
21) 1-(5-(2-fluoro-6-chlorophenyl)-1-((3-chlorophenyl)sulfonyl)-4-methoxy-1H-pyrrol-3-yl)-N-methylmethanamine;
22) 1-(1-((3-fluorophenyl)sulfonyl)-4-methoxy-5-(2,4,6-trifluorophenyl)-1H-pyrrol-3-yl)-N-methylmethanamine;
23) 1-(1-((3-chlorophenyl)sulfonyl)-4-methoxy-5-(2,4,6-trifluorophenyl)-1H-pyrrol-3-yl)-N-methylmethanamine;
24) 1-(1-((3-trifluoromethylphenyl)sulfonyl)-4-methoxy-5-(2,4,6-trifluorophenyl)-1H-pyrrol-3-yl)-N-methylmethanamine;
25) 1-(1-((3-methoxyphenyl)sulfonyl)-4-methoxy-5-(2,4,6-trifluorophenyl)-1H-pyrrol-3-yl)-N-methylmethanamine;
26) 1-(1-((3,4-difluorophenyl)sulfonyl)-4-methoxy-5-(2,4,6-trifluorophenyl)-1H-pyrrol-3-yl)-N-methanamine;
27) 1-(1-((3-fluorophenyl)sulfonyl)-4-methoxy-5-(2,3,6-trifluorophenyl)-1H-pyrrol-3-yl)-N-methylmethanamine;
28) 1-(1-((3-chlorophenyl)sulfonyl)-4-methoxy-5-(2,3,6-trifluorophenyl)-1H-pyrrol-3-yl)-N-methylmethanamine;
29) 1-(1-((3-trifluoromethylphenyl)sulfonyl)-4-methoxy-5-(2,3,6-trifluorophenyl)-1H-pyrrol-3-yl)-N-methylmethanamine;
30) 1-(1-((3-methoxyphenyl)sulfonyl)-4-methoxy-5-(2,3,6-trifluorophenyl)-1H-pyrrol-3-yl)-N-methylmethanamine;
31) 1-(5-(2,5-difluorophenyl)-1-((3-fluorophenyl)sulfonyl)-4-methoxy-1H-pyrrol-3-yl)-N-methylmethanamine;
32) 1-(5-(2,5-difluorophenyl)-1-((3-trifluoromethylphenyl)sulfonyl)-4-methoxy-1H-pyrrol-3-yl)-N-methylmethanamine; and
33) 1-(5-(2,5-difluorophenyl)-1-((3-methoxyphenyl)sulfonyl)-4-methoxy-1H-pyrrol-3-yl)-N-methylmethanamine.

13. The compound or a pharmaceutically acceptable salt thereof according to claim 1, wherein the pharmaceutically acceptable salt is hydrochloride or fumarate salt.

14. A pharmaceutical composition for the treatment of gastrointestinal damage due to gastrointestinal tract ulcer, gastritis, reflux esophagitis or *H. pylori*, comprising the compound or the pharmaceutically acceptable salt thereof according to claim 1.

15. A pharmaceutical composition for the treatment of 5-HT receptor-mediated or muscarinic acetylcholine receptor-mediated diseases, comprising the compound or the pharmaceutically acceptable salt thereof according to claim 1.

16. The pharmaceutical composition according to claim 15, wherein the 5-HT receptor-mediated or muscarinic acetylcholine receptor-mediated diseases are depression, manic depression, schizophrenia, autism, obsessive-compulsive neurosis, anxiety disorder, migraine, hypertension, eating disorder, irritable bowel syndrome (IBS), peptic ulcer, diabetic neuropathy, asthma, and overactive bladder.

* * * * *